United States Patent [19]
Tiernan et al.

[11] Patent Number: 6,150,809
[45] Date of Patent: Nov. 21, 2000

[54] GIANT MAGNETORESTIVE SENSORS AND SENSOR ARRAYS FOR DETECTION AND IMAGING OF ANOMALIES IN CONDUCTIVE MATERIALS

[75] Inventors: Timothy C. Tiernan, Santa Fe; Raymond L. Jarratt, Jr., Los Lunas, both of N. Mex.

[73] Assignee: TPL, Inc., Albuquerque, N. Mex.

[21] Appl. No.: 08/932,843

[22] Filed: Sep. 18, 1997

Related U.S. Application Data

[60] Provisional application No. 60/026,424, Sep. 20, 1996.

[51] Int. Cl.[7] ............................ G01N 27/82; G01R 33/09
[52] U.S. Cl. .......................... 324/238; 324/235; 324/225; 324/252
[58] Field of Search .................................. 324/238, 239, 324/207.21, 252, 235, 225, 228, 234, 260, 262

[56] References Cited

U.S. PATENT DOCUMENTS

| | | |
|---|---|---|
| 3,449,664 | 6/1969 | Smith . |
| 3,450,986 | 6/1969 | Chapman et al. . |
| 4,495,466 | 1/1985 | Lakin . |
| 4,677,379 | 6/1987 | Arnaud et al. . |
| 4,916,392 | 4/1990 | Sendeff et al. . |
| 5,036,277 | 7/1991 | van der Walt . |
| 5,298,858 | 3/1994 | Harrison . |
| 5,336,998 | 8/1994 | Watts et al. . |
| 5,399,968 | 3/1995 | Sheppard et al. . |
| 5,442,508 | 8/1995 | Smith . |
| 5,465,185 | 11/1995 | Heim et al. . |
| 5,475,304 | 12/1995 | Prinz . |
| 5,491,409 | 2/1996 | Flora et al. ............................ 324/238 |
| 5,510,709 | 4/1996 | Hurley et al. . |
| 5,554,933 | 9/1996 | Logue . |
| 5,561,368 | 10/1996 | Dovek et al. . |
| 5,565,236 | 10/1996 | Gambino et al. . |

FOREIGN PATENT DOCUMENTS 0030943  2/1982  Japan ..................................... 324/238

*Primary Examiner*—Jay M. Patidar
*Attorney, Agent, or Firm*—Rod D. Baker

[57] ABSTRACT

An apparatus and method for detecting defects in electrically conductive materials. A detection method and apparatus are provided for using applied magnetic fields to induce magnetic fields in the material under test, and then directly detecting changes in the induced magnetic field attributable to corrosion, cracks, flaws, or anomalies in the material under test. The invention features the use of one or more giant magnetoresistance sensors to detect directly the changes in the induced magnetic field, which changes provoke a response in the giant magnetoresistance sensors in the form of a change in resistance signal. The apparatus may be configured in various ways, including absolute field detection and differential field detection configurations, with either passive or active field compensation, and single sensor or multiple sensor arrays. A plurality of giant magnetoresistance sensors may be disposed upon a single substrate, or on multiple substrates. The invention includes method for performing detection by use of giant magnetoresistance.

24 Claims, 31 Drawing Sheets

GIANT MAGNETORESTIVE SENSORS AND SENSOR ARRAYS FOR DETECTION AND IMAGING OF ANOMALIES IN CONDUCTIVE MATERIALS

CROSS-REFERENCE TO RELATED APPLICATIONS

This application claims the benefit of the filing of Provisional Application Ser. No. 60/026,424, entitled "GMR-Based Sensor For Detection of Defects in Conductive Materials," filed on Sep. 20, 1996, and the specification thereof is incorporated herein by reference.

GOVERNMENT RIGHTS

The Government has rights to this invention pursuant to Award No. DM-95-60415 awarded by the U.S. National Science Foundation.

BACKGROUND OF THE INVENTION

1. Field of the Invention

This invention relates to an apparatus and method for detecting magnetic fields, particularly detecting magnetic fields using giant magnetoresistance sensors, and specifically the use of giant magnetoresistance sensors to detect magnetic fields to perform non-destructive evaluation of electrically conductive components.

2. Description of Prior Art

A variety of methods currently are used to perform non-destructive evaluation (NDE) of anomalies and stresses in metal structures used in buildings, bridges, and aircraft components. Known techniques of NDE are based upon visual inspections, eddy current, X-ray radiography, ultrasonics, and acoustic emissions. These methods suffer from limitations in inspection capability, speed of inspection, and cost of inspection. Although they have some of the same limitations as known NDE methods, newer techniques such as holography, thermography, and shearography have shown some promise in laboratory testing. However, no known commercially viable inspection system based upon these more sophisticated technologies has yet been developed.

Giant magnetoresistance (GMR) is an effect characterized by large changes in resistance of certain types of materials in response to the presence of a magnetic field. With GMR, there is a "giant" change in resistance ($\Delta R/R$) response that is markedly greater in magnitude than that obtained by ordinary anisotropic magnetoresistance (AMR) effects. Generally, materials and components observed to exhibit giant magnetoresistance consist of multiple layers of very thin (roughly 20 Angstrom) ferromagnetic film alternated with similarly thin layers of non-magnetic conducting films, typically of copper, cobalt, nickel, iron and other metals. There have also been reports of GMR materials made using powders as starting materials.

There are known methods for exploiting the GMR effect to sense magnetic field changes. U.S. Pat. No. 5,465,185, for example, describes a type of sensor made with GMR material oriented in a particular way to form a so-called "spin valve" sensor. Spin valve sensors can be fabricated as shown in U.S. Pat. No. 5,561,368, to compensate for the offset inherent in these devices when DC measurements are made. In addition to spin valves, there are a number of different ways to make other GMR materials and sensors (i.e. tunnel junction and other named device structures) using a variety of materials and physical orientations. U.S. Pat. No. 5,565,236, describes a method for making a type of GMR sensor.

GMR sensors have been widely investigated for application in magnetic detection heads (for reading binary data stored on the disks) for hard disk drives. The great potential of GMR sensors as magnetoresistive heads stems from the very large maximum change in resistance ($\Delta R/R$ as much as 10–20% in some systems) that they can exhibit in response to magnetic fields, as compared to the $\Delta R/R$ of 2% typical of known magnetoresistant films employing the usual AMR effect. U.S. Pat. No. 5,442,508 describes a GMR sensor used as a reproduction head.

In general, GMR films are in a high resistance state when the magnetization in the GMR multilayer is predominantly antiparallel in adjacent magnetic layers, and can be then brought to a low resistance state by the action of an applied field which rotates the layers' magnetization into a predominantly parallel orientation roughly along the applied field direction. Consequently, GMR sensors generate a signal, based on a change in resistance, in response to a change in an external magnetic field.

One known application of GMR sensors is to measure linear displacement. U.S. Pat. No. 5,475,304 describes a GMR sensor and apparatus for measuring linear and angular displacement particularly for use in high precision machining applications.

A variety of sensors presently are used in eddy current systems for NDE of electrically conductive objects. Eddy current systems that use an excitation coil for inducing an alternating magnetic field in an object, and a pick-up coil for detecting the magnetic field induced, are widely used for detecting defects or anomalies in metallic materials. This kind of eddy current system detects a flaw by detecting the metal loss due to the flaw. The flaw or crack in the metal disrupts the normal eddy current fields. This disruption of eddy currents changes the magnetic fields, which change is detected by variations in the inductance of the pick-up coil. Conventional eddy current equipment, with cup core type probes, is intended for the detection of large cracks emanating from fastener holes in second or interior layers. Cup core probes interrogate the entire fastener hole during inspection and consequently are not very sensitive to the presence of small cracks.

U.S. Pat. No. 3,449,644 describes a magnetic reaction testing device and method of testing utilizing a semiconductor means for magnetic field sensing of an eddy-current-reaction magnetic field. The device is specific exclusively to pairs of Hall effect detectors. The relative field strength mode of operation requires placement of large sensors outside the excitation coil and detects the variation between at least one pair of angularly separated detectors.

U.S. Pat. No. 3,450,986 describes a magnetic reaction testing device and method of testing utilizing semiconductor means for magnetic field sensing of an eddy-current-reaction magnetic field. A single sensor absolute field detector, a variation of the device shown in U.S. Pat. No. 3,449,644, is described. The specific use of a Hall effect absolute field detector requires sensor placement outside the excitation coil.

U.S. Pat. No. 4,495,466 describes an eddy current test probe with circumferential segments and a method of testing material surrounding fastener holes. The disclosed detection method is common to known coil-based eddy current detectors, having output proportional to defect area divided by total excitation area. A multipole ferrite cup is used for magnetic field concentration around the hole under inspection. This sensor involves multiple, complex windings specific to a given hole size, and is extremely sensitive to field distortion due to off-center location errors.

U.S. Pat. No. 4,677,379 describes a process and device for detecting cracks in riveted joints using an eddy current probe. The disclosed device uses a four coil quadrature sensor configuration with synchronous detector to determine asymmetry in a uniform excitation field due to elongation along a crack. The size and optimum diameter of the device's sensor arrangement must be equal to rivet spacing, and the four coils must be precisely matched.

U.S. Pat. No. 5,399,968 describes an eddy current probe, having a body of high permeability supporting drive coil and plural sensors, very similar to the device of U.S. Pat. No. 4,495,466 with the addition of an outer winding to provide deeper field penetration, the possibility of a rectangular structure in addition to the simple pot core, and the possibility of Hall sensors at each pole. The disclosed device is extremely sensitive to field distortion due to off center location errors of the sensors.

U.S. Pat. No. 5,510,709 describes an eddy current surface inspection probe and method for aircraft fastener inspection. The device uses a circular array of coil pairs to produce a differential output signal. The largest output signal indicates the axis of the anomaly, and total output indicates the relative size of the defect. The size of the sensor array must be matched to the size of the rivet under inspection, making it extremely sensitive to field distortion due to off center location errors.

U.S. Pat. No. 4,916,392 describes a contactless current control sensor device for magnetoelectric crack detection. A movable sensor or a line of fixed sensors is used to measure the radial field variation around a conductor carrying a fixed test current. Anomalies in the radial field are then associated with disruptions in uniform current flow presumably due to cracks in the conductor. The disclosed device requires that the defective sample carry stable fixed test currents of 10 to 20,000 Amps, and variations in conductivity or conductor dimensions are indistinguishable from crack effects.

U.S. Pat. No. 5,298,858 teaches a device for non-destructive testing of electrically conductive materials. The device uses square wave excitation to generate wide band eddy current pulse echos, and synchronously gates a detection window to isolate echos from regions of interest. The device is directed to the use of a circular magnetic field for fixed radius circular scans, presumably for fasteners. Second, it is extremely sensitive to off-center sensor location errors; data must be time-shift corrected at each separate sample point to correct for off center errors.

U.S. Pat. No. 5,554,933 describes a polar coordinates sensor probe for testing material surrounding fastener holes using multipole ferrite cup detector essentially similar to the device of U.S. Pat. No. 4,495,466. The disclosed device uses a separate toroidal coil to produce a directed field component which sweeps around a ferrite cup, ostensibly increasing the relative field in the vicinity of a defect compared to the total applied field. A separate toroidal coil, much larger than the ferrite cup detector is used causing difficulty in producing a uniform rotating field.

An article written by William F. Arvin of Quantum Magnetics, Inc. and published in the Review of Progress in Quantitative Nondestructive Evaluation, vol. 15, Plenum Press, New York, 1996, describes magnetoresistive eddy current sensors for detecting deeply buried flaws. The article discusses magnetoresitors and SQUID (superconducting quantum interference device) sensors. It does not specifically discuss giant magnetoresistance sensors and makes no mention of sensor arrays.

Most of the foregoing references disclose devices employing coil-type sensors or Hall effect sensors, which are unlike magnetoresistors or giant magnetoresistors. Those that do mention the use of magnetoresistance refer to older types of devices that do not have the properties of giant magnetoresistance.

A need remains, thus, for an apparatus and method of performing NDE which provides rapid inspection capability, the ability to detect a variety of anomalies including corrosion, cracks, and stresses both at the surface and deep inside both simple and complex parts, can be fabricated in a high-density array and which is simple to use, eliminating the need of a highly trained, highly paid operator, particularly in the performance of maintenance or in-service inspections (as opposed to production quality inspection).

The present invention fills this unmet need by using a GMR sensor in the detection apparatus or method. The use of GMR sensors is not an obvious extension of other types of sensors including conventional magnetoresistors because, among other reasons, GMR sensors require special orientations in magnetic fields to exploit the effects of giant magnetoresistance and can be fabricated in high-density 2- and 3-dimensional arrays. Accordingly, the present invention makes novel use of specific types of differential detection and self-nulling and/or self-biasing operations.

SUMMARY OF THE INVENTION

According to the invention there is provided an apparatus for performing non-destructive evaluation of a material. The apparatus comprises at least one magnetic field generator for applying a magnetic field to the material, thereby inducing in the material an induced magnetic field, at least one giant magnetoresistance sensor proximate to the generator means and responsive to the induced magnetic field, and some means for detecting changes in resistance in the giant magnetoresistance sensor. The giant magnetoresistance sensor(s) has a sensitive axis and preferably comprise alternating layers of a ferromagnetic substance and a non-magnetic electrically conductive substance. The preferred means for detecting changes in resistance in the giant magnetoresistance sensor is either an RMS meter or an analog-to-digital converter, or both. Preferably, the field generator is an electrically conductive coil having a principal axis. Alternatively, the field generator is a conductive winding wrapped about a ferrite core. The sensitive axis of the GMR sensor may be disposed substantially orthogonal to the principal axis of the coil, whereby said sensitive axis is unaligned with said applied magnetic field, or may be disposed substantially parallel to the principal axis of said coil, whereby the sensitive axis is substantially aligned with the applied magnetic field. The giant magnetoresistance sensor may be disposed substantially at an end of the coil, or may be disposed substantially interior to the coil.

Alternative embodiments of the apparatus of the invention include means for generating a compensative magnetic field counteractive to the applied magnetic field, and means for driving the means for generating a compensative magnetic field with a response from the giant magnetoresistance sensor. In these embodiments, the means for driving the means for generating a compensative magnetic field comprises a fast current amplifier in communication with the giant magnetoresistance sensor, and a voltage sensor in communication with the fast current amplifier, and further includes means, in communication with the voltage sensor, for monitoring a drive voltage input into the fast current amplifier.

The field generator preferably comprises an electrically conductive coil having a principal axis, and the sensitive axis may be disposed substantially parallel to the coil's principal axis. One means for generating a compensative magnetic field comprises a compensation coil disposed coaxially within the conductive coil and disposed around the giant magnetoresistance sensor. Alternatively, the field generator comprises a substantially planar conductive drive sheet and the means for generating a compensative magnetic field comprises a substantially planar conductive compensating sheet substantially parallel to the drive sheet, with the giant magnetoresistance sensor disposed between the two conductive sheets.

When the field generator is a ferrite core with conductive winding, the apparatus of the invention alternatively comprises at least two giant magnetoresistance sensors surrounded by the ferrite core, with the sensitive axis of at least one of the magnetoresistance sensors disposed substantially perpendicular to a sensitive axis of at least one other of the magnetoresistance sensors. In this alternative embodiment, the apparatus may include a circuit means for summing responses from at least two giant magnetoresistance sensors, an optional RMS detector for receiving a voltage signal from the summing circuit, and a converter means for converting the voltage signal into a digital signal. Or, this embodiment may include circuit means for detecting a difference in magnitudes of response from least two giant magnetoresistance sensors, an optional RMS detector for receiving a voltage signal from the circuit means for detecting, and some converter for converting said voltage signal into a digital signal.

Also according to the invention, there is provided a plurality of giant magnetoresistance sensors disposed upon at least one substrate, and the substrate optionally comprises a flexible material. Also, a plurality of magnetoresistance sensors may be disposed upon a plurality of substantially parallel substrates.

The invention includes elements for processing signals (i.e. changes in resistance) from GMR sensors incorporated in the apparatus. Accordingly, there is provided by the invention an apparatus comprising at least one magnetic field generator means for applying a magnetic field to the material, thereby inducing in the material an induced magnetic field, at least one giant magnetoresistance sensor proximate to the generator means and directly responsive to the induced magnetic field, the sensor having a sensitive axis, and means for detecting changes in resistance in the at least one giant magnetoresistance sensor due to the induced magnetic field. The means for detecting changes in resistance may comprise means for directly processing signals from the giant magnetoresistance sensor. The means for directly processing signals may comprise an amplifier for amplifying signals from the giant magnetoresistance sensor, a true RMS detector in communication with the amplifier, and an analog-to-digital converter in communication with the RMS detector. Alternatively, the means for directly processing signals may comprise an amplifier for amplifying signals from the giant magnetoresistance sensor, a magnitude and phase detector in communication with the amplifier, and an analog-to-digital converter in communication with the magnitude and phase detector. Alternative embodiments may further comprise a means for generating a compensative magnetic field counteractive to the applied magnetic field, and a fast current amplifier, in communication with the giant magnetoresistance sensor, for driving the compensative magnetic field generator with a response from the giant magnetoresistance sensor, in which embodiment the means for detecting changes in resistance comprises a voltage sensor in communication with the fast current amplifier; and means, in communication with the voltage sensor, for monitoring a drive voltage input into the fast current amplifier. The applied field generator optionally is a conductive winding wrapped about a ferrite core, in which case the at least one giant magnetoresistance sensor preferably comprises at least two giant magnetoresistance sensors surrounded by the ferrite core, with the sensitive axis of at least one of the giant magnetoresistance sensors disposed substantially perpendicular to a sensitive axis of at least one other of the giant magnetoresistance sensors. In this embodiment of the invention, the means for detecting changes in resistance preferably comprises circuit means for summing responses from the at least two giant magnetoresistance sensors, an RMS detector for receiving a voltage signal from the circuit means for summing, and a converter means for converting the voltage signal into a digital signal. Alternatively, the means for detecting changes in resistance comprises a circuit for detecting a difference in magnitudes of response from the at least two giant magnetoresistance sensors, an RMS detector for receiving a voltage signal from the circuit for detecting, and a converter means for converting the voltage signal into a digital signal.

Also according to the invention there is provided a method for performing non-destructive evaluation of a material, the method comprising applying a magnetic field to the material, thereby inducing in the material an induced magnetic field, locating adjacent to the material at least one giant magnetoresistance sensor responsive to the induced magnetic field; and detecting changes in resistance in the giant magnetoresistance sensor.

BRIEF DESCRIPTION OF THE DRAWINGS

Other objects advantages and features of the present invention will become apparent from the following specification when taken together with the accompanying drawings in which the elements are enumerated and in which:

FIG. 2b is a top sectional view of the embodiment of FIG. 2a;

FIG. 4b is a top sectional view of the embodiment of FIG. 4a;

FIG. 5b is a top sectional view of the embodiment of FIG. 5a,

FIG. 7b is a top sectional view of the embodiment of FIG. 7a;

FIG. 9b is a bottom view in partial section of the embodiment of FIG. 9a;

FIG. 11b is a side sectional view of the embodiment of FIG. 11a;

FIG. 13b is a side sectional view of the embodiment of FIG. 13a;

DETAILED DESCRIPTION OF THE PREFERRED EMBODIMENTS

Figure 1A:
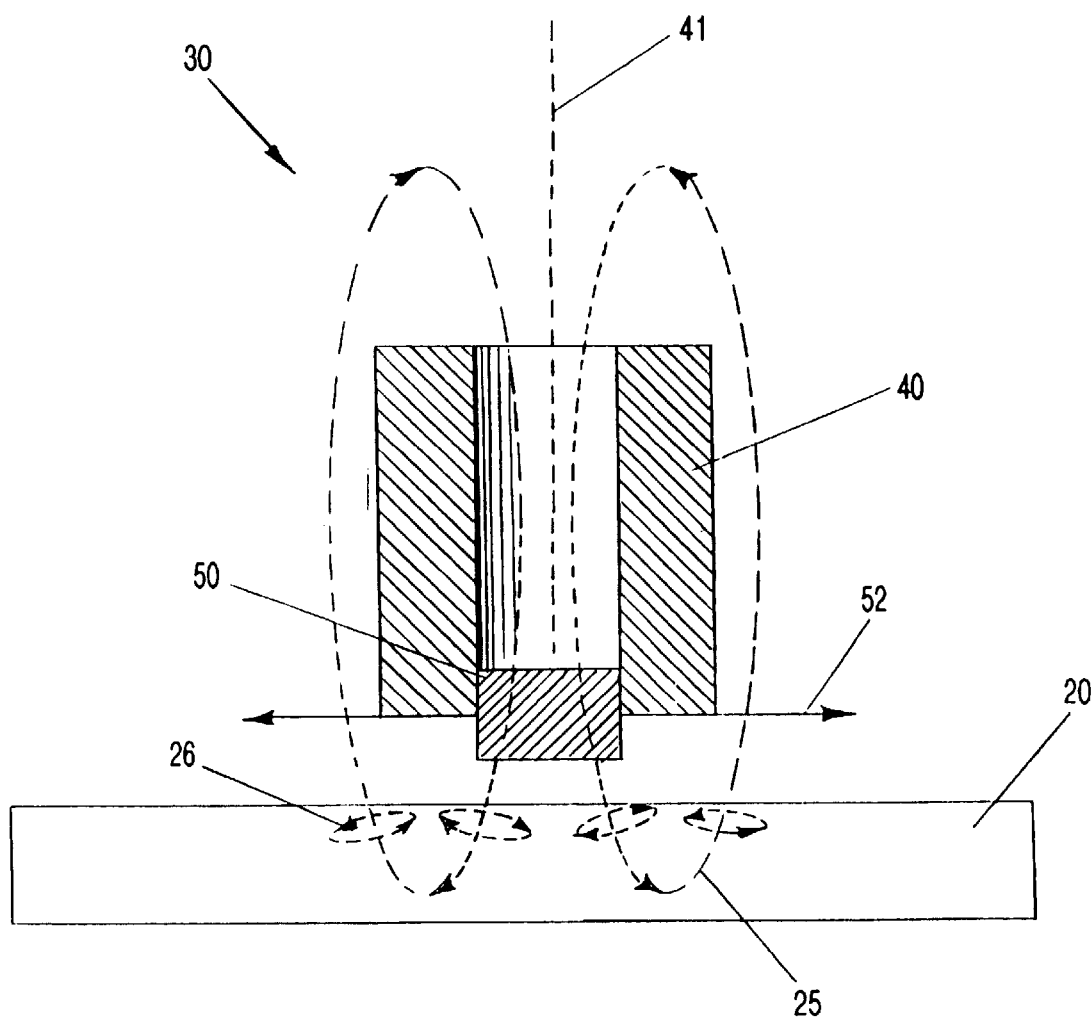
FIG. 1a is a schematic view of one embodiment of the invention disposed in the differential sensor configuration.

This invention relates to the use of magnetic field detection to perform non-destructive evaluation of conductive, typically but not necessarily metallic, components. In the disclosure and claims, "conductive" means electrically conductive unless otherwise indicated. By means of the invention, changes in magnetic field attributable to flaws or discontinuities in the sampled component or structure may be detected without having to dis-assemble or destroy the component. The present invention uses one or more giant magnetoresistance sensors directly to detect a magnetic field induced in the material to be tested. It will be readily apparent that the invention finds beneficial application for corrosion and crack detection in metallic parts, eddy current measurements applied to NDE, manufacturing or other purposes. It is also useful for measurements related to thickness of films on metals including, but not limited to, paint thickness measurements. The invention is useable in manufacturing when flaws, pilot holes, and the presence of a material must be determined. The invention has applications in both chemistry and medicine, including uses in nuclear magnetic resonance (NMR) and magnetic resonance imaging (MRI).

The giant magnetoresistance (GMR) phenomenon is a recently discovered effect occurring in metallic films consisting of magnetic layers a few nanometers thick separated by equally thin nonmagnetic layers. Large changes in the resistance of these films is observed when an external magnetic field is applied. The cause of this effect is the spin dependence of electron scattering and the spin polarization of conduction electrons in ferromagnetic metals. With layers of the proper thickness, adjacent magnetic layers couple antiferromagnetically to each other with the magnetic moments of each magnetic layer aligned antiparallel to the adjacent magnetic layers. Conduction electrons, spin polarized in one magnetic layer, are likely to be scattered as they reach the interface with an adjacent magnetic layer with antiparallel conduction electron spins. Frequent scattering results in high resistivity. However, if an external field overcomes the antiferromagnetic coupling and compels parallel alignment of moments in adjacent ferromagnetic layers, the spin dependent scattering of conduction electrons is decreased and resistivity decreases. The size of this decrease in resistivity can be 10% to 20% and higher in GMR materials with multiple nonmagnetic layers.

Known systems utilizing eddy current sensors excite a drive coil and sense impedance changes in a coil due to induced eddy currents in a material under test (MUT). The detector of the present invention is significantly different from known eddy current sensors in that, among other differences, a GMR sensor detects induced field changes directly, rather than indirectly. Any changes in excitation field amplitude due to eddy current field interaction with the excitation coil adversely affects the information content in the detected output signal. An increase in eddy current field strength produces an increase in sensor output and also an increase in the impedance of the excitation winding. To prevent the increased excitation winding impedance from reducing the excitation field and consequently the sensor output, an impedance insensitive, constant field strength excitation circuit may be employed in the invention. This may be accomplished by using a constant amplitude sine wave signal to drive a precision wide band voltage to current converter with a current source impedance considerably in excess of the excitation coil impedance.

The depth of penetration of a magnetic field into a material under test can be controlled by transducer geometry and signal frequency. A computer-controlled array of GMR sensors, tuned to the magnetic field frequency, can be used to scan large areas of a component rapidly with a high degree of spatial resolution. Data from the scanned area may be used to construct an image viewable on a portable video monitor, making possible the rapid detection of small anomalies in a variety of metallic components or structures. In addition, it is possible to correlate measured magnetic field properties with mechanical properties of the sampled structure, permitting on-site assessment of failure probability. The combination of excellent signal to noise ratio, high spatial resolution, and depth profiling of the invention results in an NDE technology superior to existing systems, such as those based on conventional eddy current technologies and other technologies.

Figure 1B:
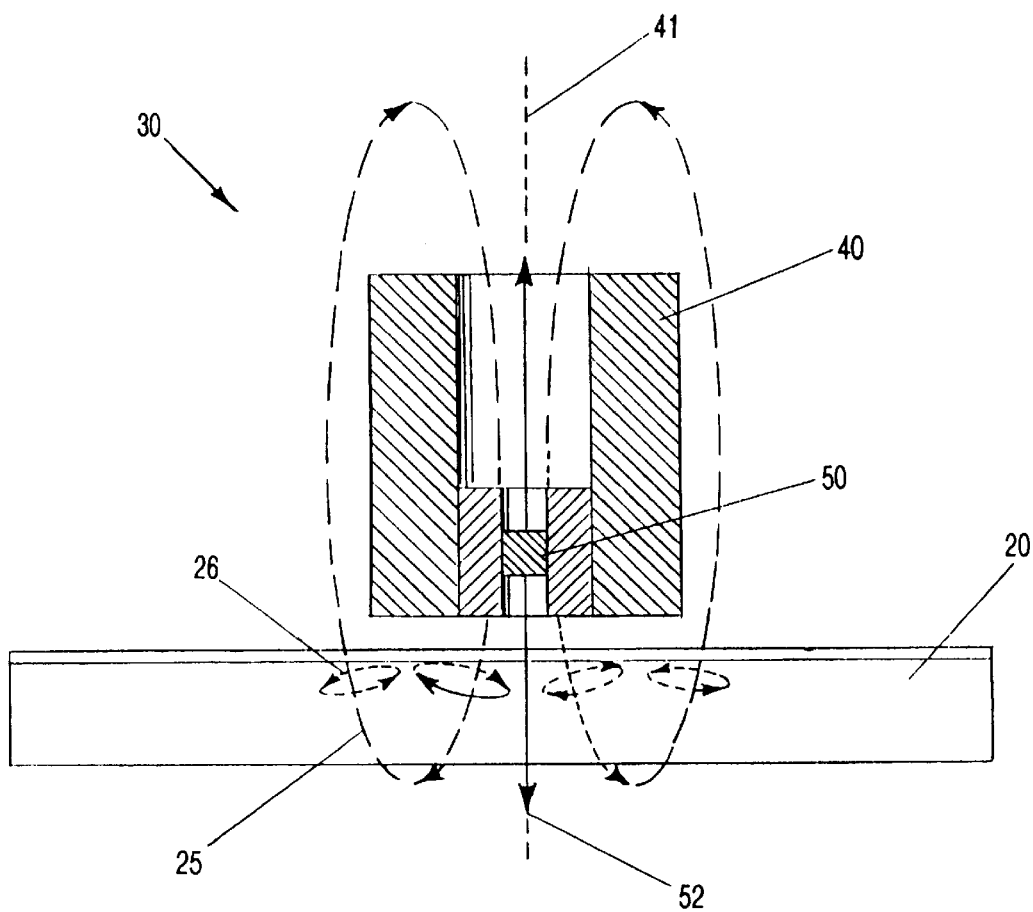
FIG. 1b is a schematic view of an alternative embodiment of the invention disposed in the absolute sensor configuration.
Figure 15:
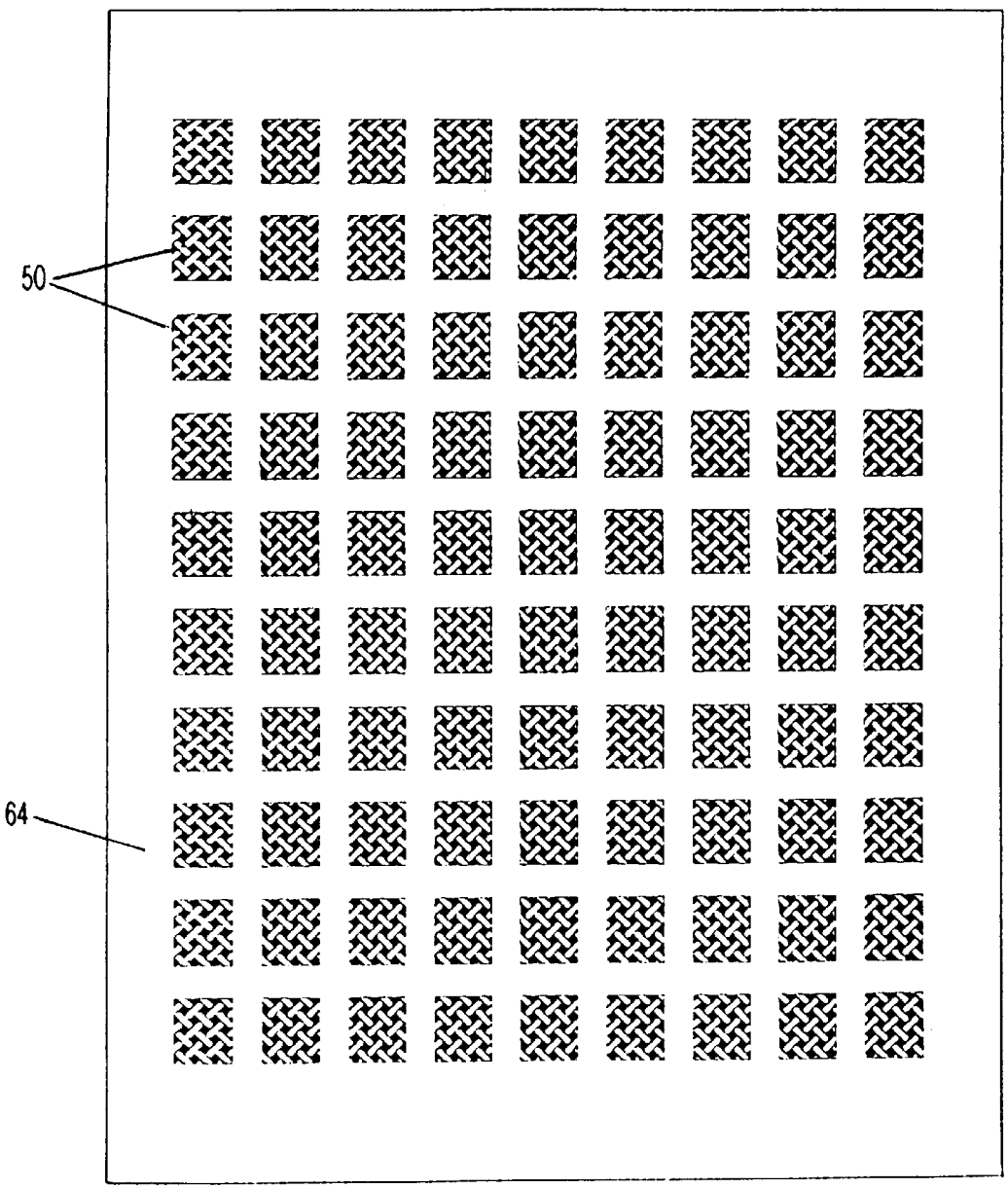
FIG. 15 depicts a two dimensional array of GMR sensors on a single substrate useable in the apparatus of the invention.
Figure 16:
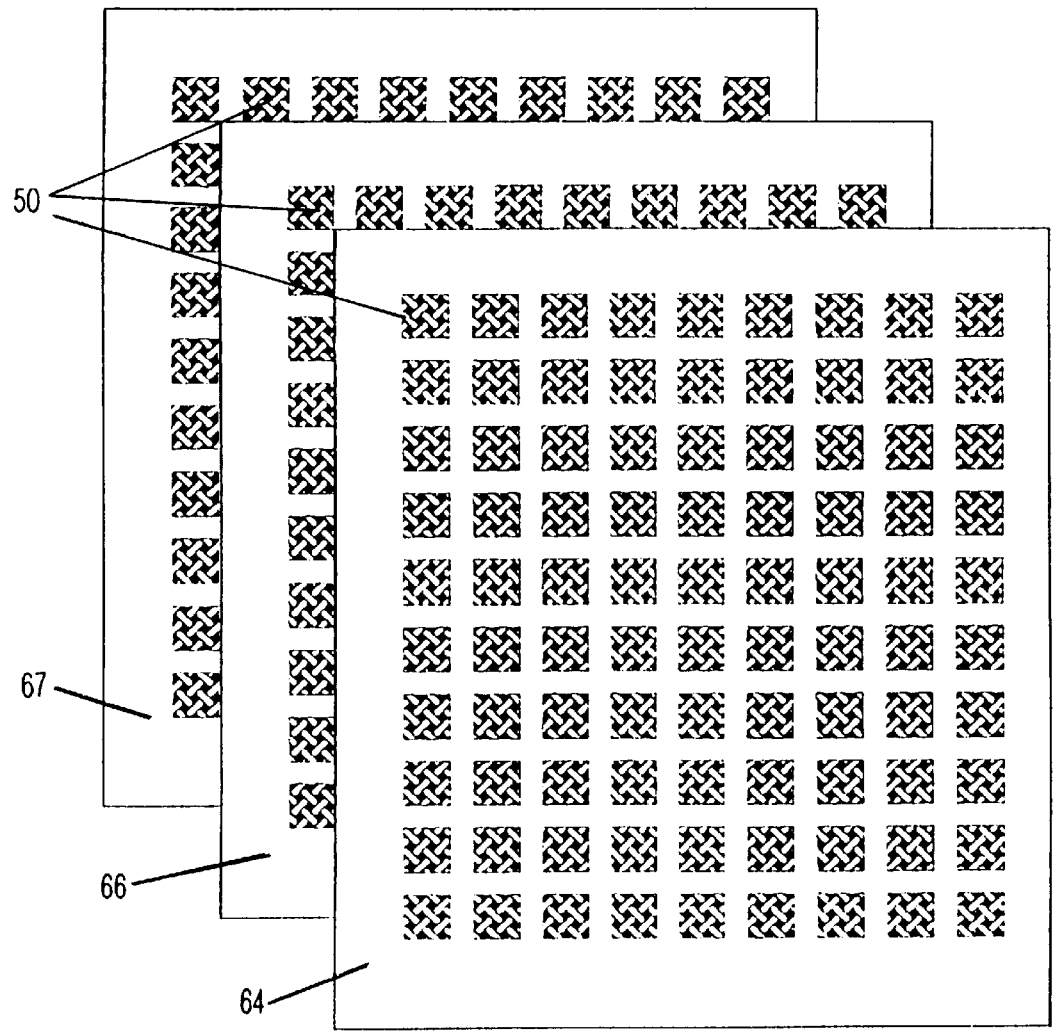
FIG. 16 depicts a three dimensional array of GMR sensors on a plurality of substrates useable in the apparatus of the invention.

FIG. 1a illustrates a basic differential sensor configuration of the detector apparatus 30 of the present invention. FIG. 1b shows an alternative, also basic, absolute sensor configuration of the detector apparatus 30 of the invention. Both configurations can be adapted to use single sensor element or sensor array-based systems. The GMR sensor 50 is a magnetic field-dependent resistance element usable singly, or in a shielded Wheatstone bridge configuration, or in a two- or three-dimensional array of sensor elements (FIGS. 15 and 16). Each GMR sensor 50 responds to permanent magnets, electromagnets, the earth's magnetic field for low field NMR measurements, or any other source of magnetic fields. In all embodiments of this invention, the source of the applied magnetic filed may simply be the earth's magnetic field; thus, the earth itself may be a natural means for generating an applied magnetic field.

Reference is made to FIGS. 1a and 1b. In a GMR sensor 50, maximum sensor output occurs for fields originating along the "easy" or most sensitive axis 52 indicated by a directional arrow in FIGS. 1a and 1b. Response along the antiparallel "hard" axis is low, and response out of the plane of the GMR sensor 50 is very low. The present invention makes use of all the foregoing attributes.

The differential configuration shown in FIG. 1a detects the induced magnetic field 26 orthogonal to the applied magnetic field 25. An electrically driven coil or solenoid 40 (with air, ferrite or other core) is used to generate the magnetic field 25 that is applied generally perpendicular to the material under test 20 (MUT). The GMR sensor 50 is positioned either inside the coil 40 or at the end of the coil 40 nearest the MUT 20. The sensitive axis 52 of the GMR sensor 50 is aligned orthogonal to the principal axis 41 of the coil 40. With the GMR sensor 50 thus positioned, the sensitive axis 52 is not aligned with the applied field 25 generated by the coil 40. This differential sensor configuration, as shown in FIG. 1a, is best suited to the detection of cracks and pitting corrosion in the MUT 20.

The absolute configuration of the apparatus 30 shown in FIG. 1b is similar, except that the sensitive axis 52 is aligned with or parallel to the principal axis 41 of the coil 40 and thus is substantially aligned with the applied field 25. In the absolute configuration, the detector apparatus 30 can sense changes in thickness, and is well-suited to the detection of uniform, intergranular and exfoliation corrosion in the MUT 20. To prevent large applied fields from damaging the GMR sensor 50, an active-feedback, loop-filter arrangement optionally may be used.

Figure 2A:
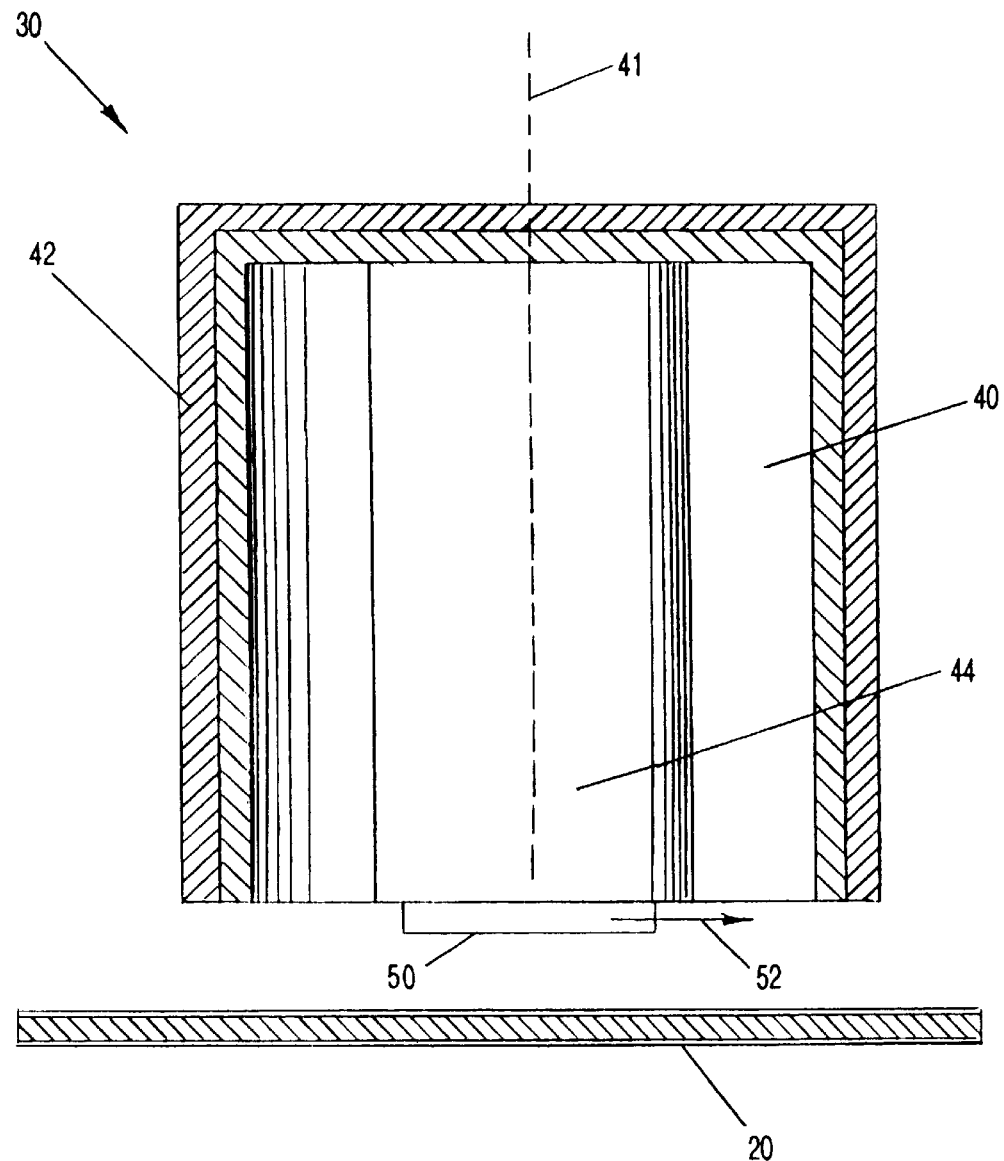
FIG. 2a is a side sectional view of a coil induction embodiment of the invention, similar to the embodiment of FIG. 1a, configured to perform differential sensing.
Figure 2B:
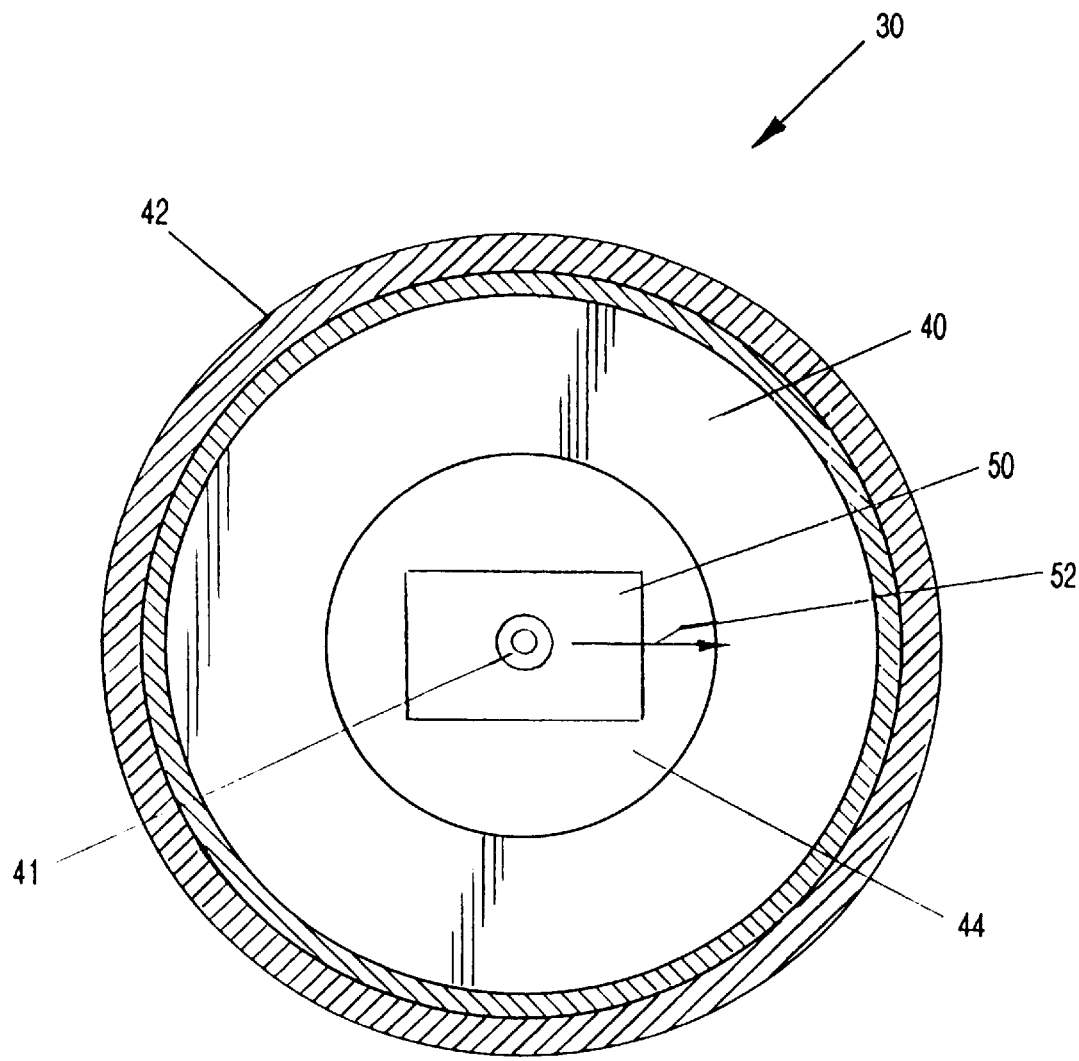
Figure 3:
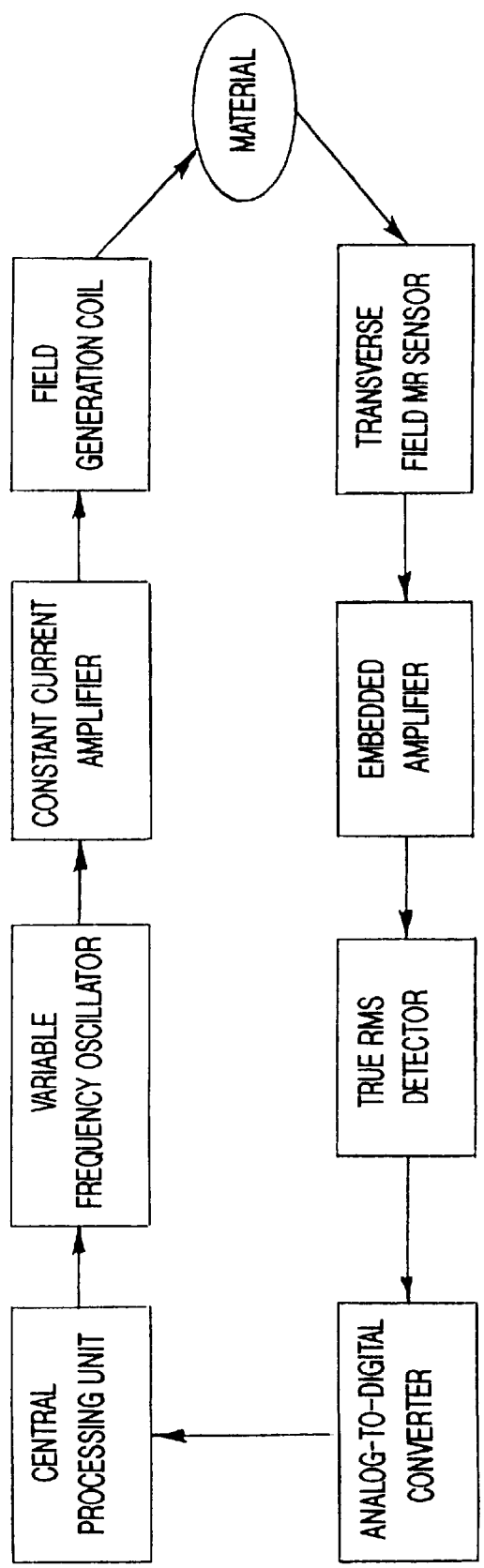
FIG. 3 is a diagrammatic illustration of the operational routine of the embodiment of FIGS. 2a and 2b.

Combined reference is made to FIGS. 2a and 2b, and 3, describing an embodiment of the detector apparatus 30 employing solenoid induction with a differential sensor configuration. In this and in all preferred embodiments, the user preferably controls the output of a variable frequency oscillator by means of a central processing unit (CPU). As best illustrated by FIG. 3, the oscillator output is converted into a constant current signal by a constant current amplifier. The constant current amplifier prevents any changes in the interrogation signal resulting from impedance changes in the coil 40 caused by the material under test (MUT) 20. The constant current amplifier drives the field generation coil 40. The coil 40 may have an air core 44 or a core 44 fashioned of phenolic material, iron, ferrite or the like. An optional flux focusing cup 42 is made from materials such as mu metal or ferrite. The principal purpose of focusing cup 42 is to confine or restrict the induction field.

FIGS. 2a and 2b illustrate that the GMR sensor 50 is at an end of the coil 40 and is placed in close proximity to the MUT 20; contact at the MUT surface closest to the GMR sensor 50 is desirable, but not necessary, and not shown in FIG. 2a for clarity of illustration. The applied magnetic field generated by the coil 40 interacts with the MUT 20. The GMR sensor 50, with its sensitive "easy" axis 52 orthogonal to the principal axis 41 of the coil 40, is positioned laterally so that the divergent components of the applied field (as seen at 25 in FIG. 1a) substantially cancel each other for self-nulling field detection, or with a finite offset for differential field detection.

The applied field generated by the coil 40 causes eddy-current flow in the MUT 20, which induces an induced magnetic field (as seen at 26 in FIG. 1a). If the MUT 20 is uniform and undamaged to a depth equal to the "skin-depth" of the MUT, the divergent components of the induced field 26 substantially cancel at the GMR sensor 50 and no signal is generated by the GMR sensor 50, in the case of self-nulling detection or a finite offset for differential field detection. The "skin-depth" of the MUT is determined from known electrical and magnetic properties of the MUT 20, as well as the selected interrogation frequency of the detector apparatus 30. However, if there is a discontinuity in the MUT 20 within the skin-depth, then the divergent components of the induced field 26 induced by the eddy current flow do not cancel, and the resistance of the GMR sensor 50 is altered, thereby sending a signal.

As indicated in FIG. 3, signaled changes in the resistance of the GMR sensor 50 are amplified by an embedded amplifier and then detected using either a True RMS meter attached to an analog-to-digital converter (A/D) or by the A/D converter directly. Alternative approaches for monitoring the output of the sensor 50 include measurements of voltage, current, resistance, impedance, and phase. The detected signal is then sent to the CPU for display to the user and optional storage within the CPU memory.

Figure 4A:
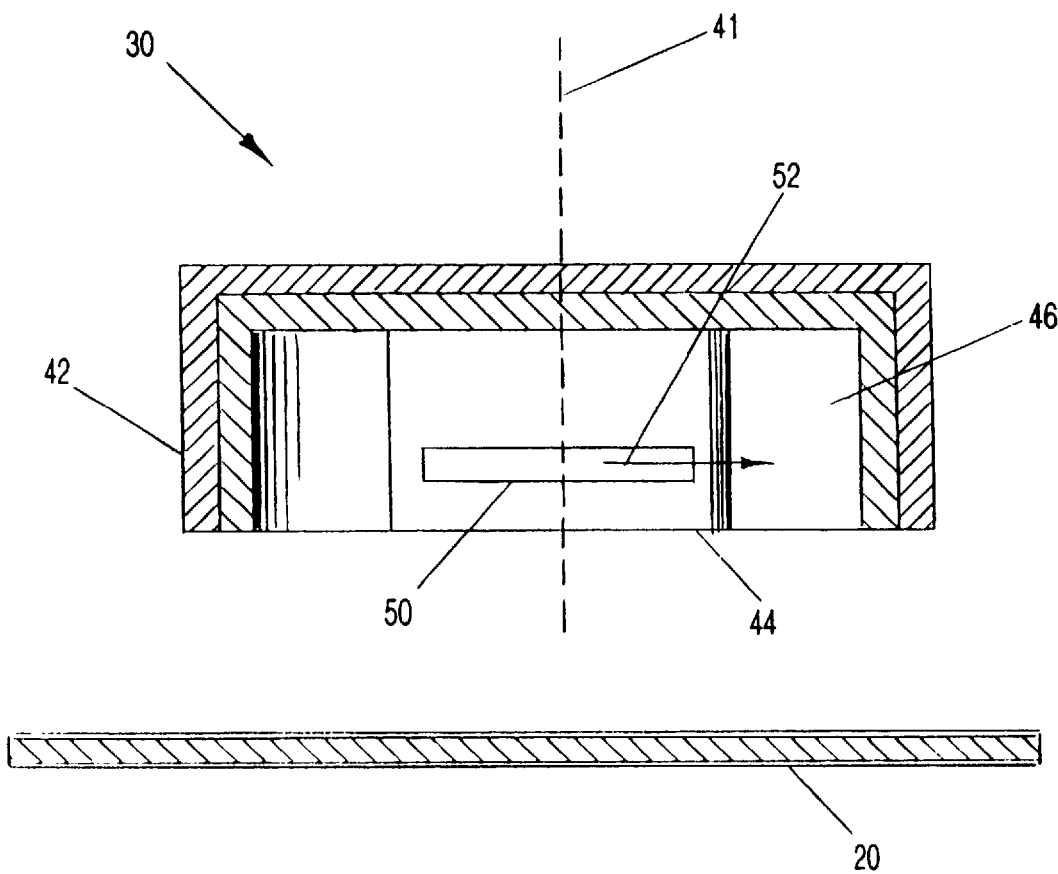
FIG. 4a is a side sectional view of a coil induction embodiment of the invention configured to perform differential sensing.
Figure 4B:
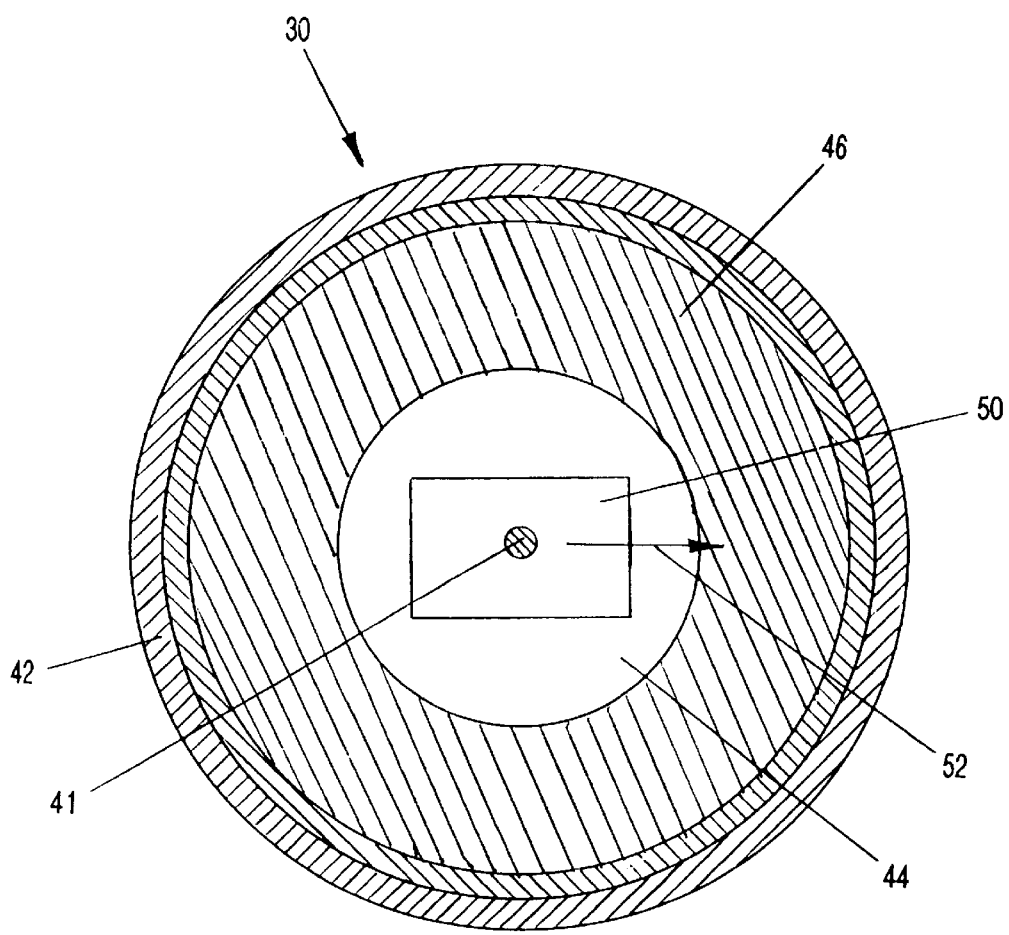

FIGS. 4a and 4b illustrate an alternative embodiment of the detector apparatus 30 employing coil induction with a differential sensor configuration. This alternative embodiment is similar to the embodiment of FIGS. 2a and 2b, except that a "pancake" coil 46 is used in place of coil 40, an air core 44 is used exclusively, the GMR sensor 50 is located interiorly within the pancake coil 46, and the optional flux focusing cup 42 covers only the top portion of the detector apparatus 30. The sensitive axis 52 is orthogonal to the principal axis 41 of the pancake coil 46; FIG. 3 also diagrams the operation routine of the embodiment of FIGS. 4a and 4b.

Figure 5A:
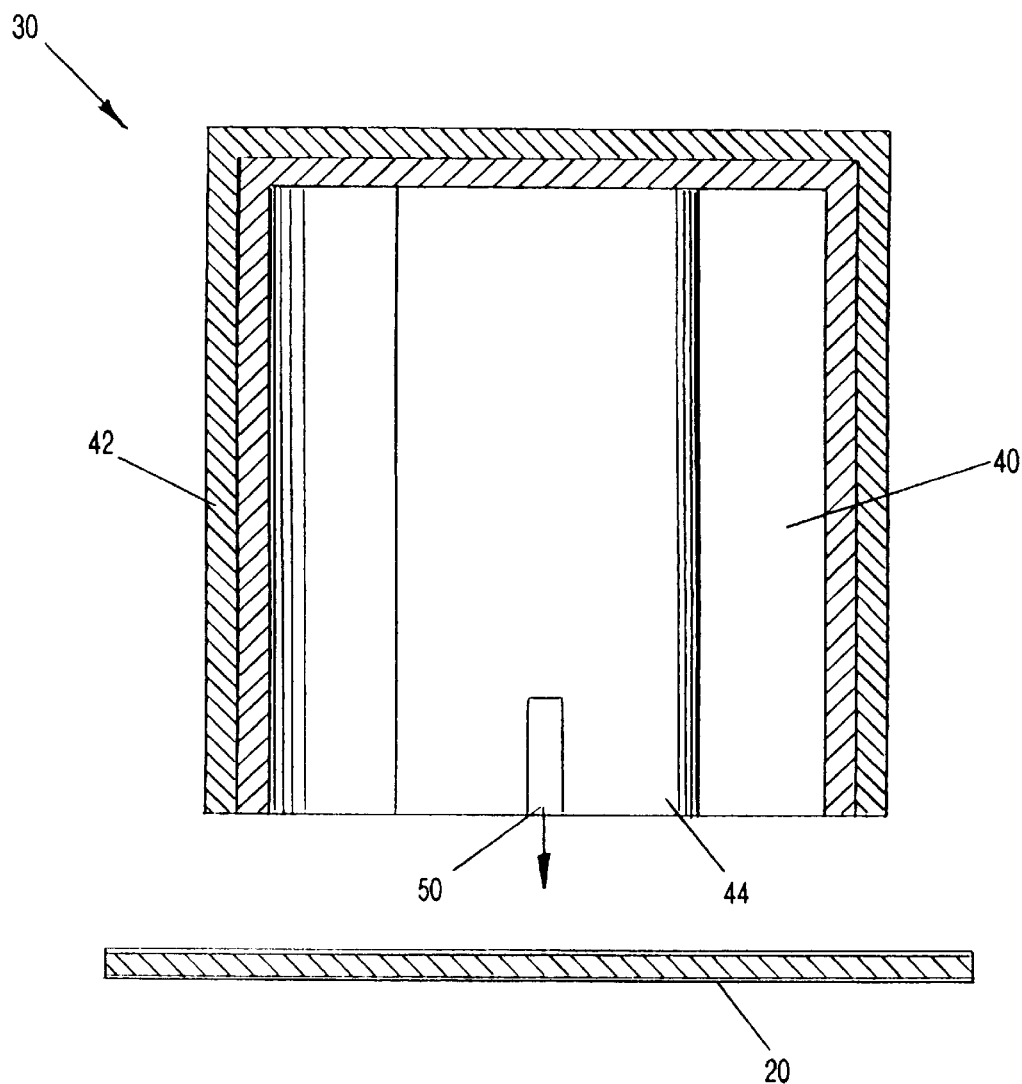
FIG. 5a is a side sectional view of a coil induction embodiment of the invention configured to perform passive absolute field sensing.
Figure 5B:
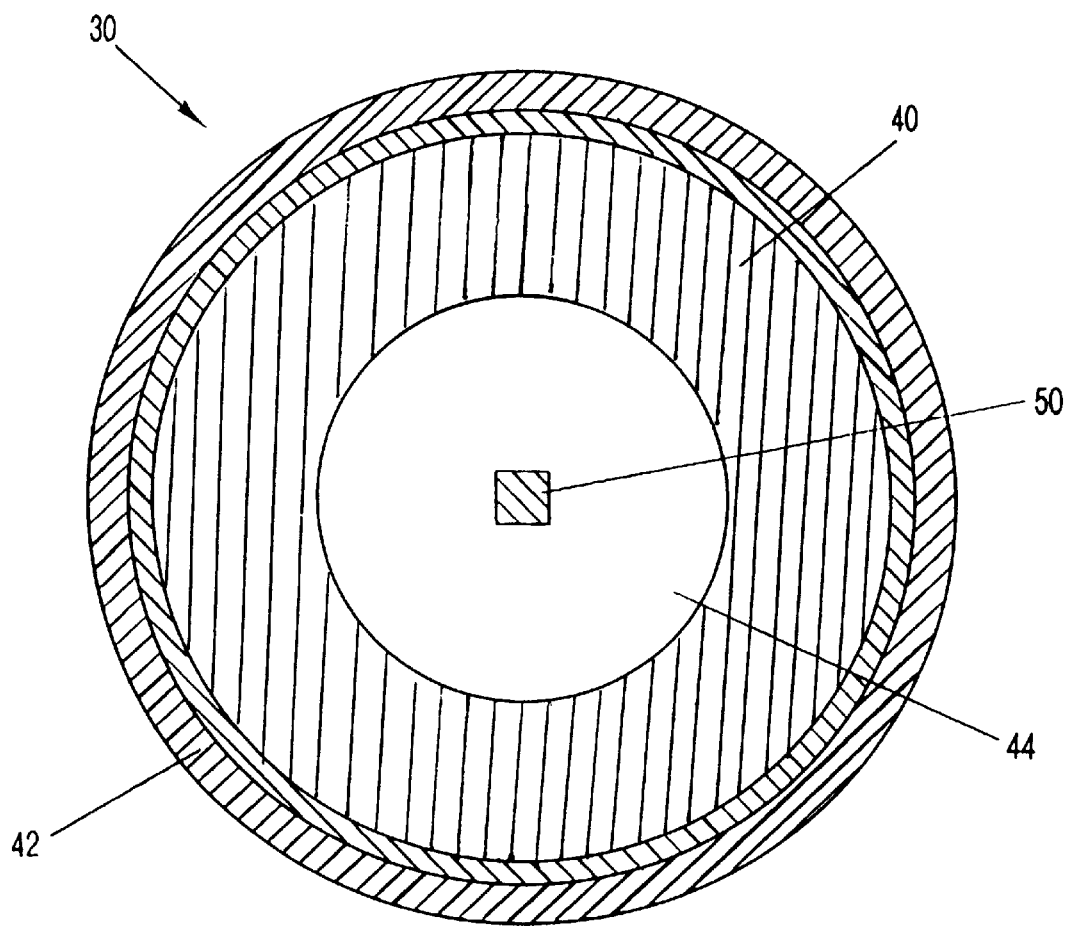
Figure 6:
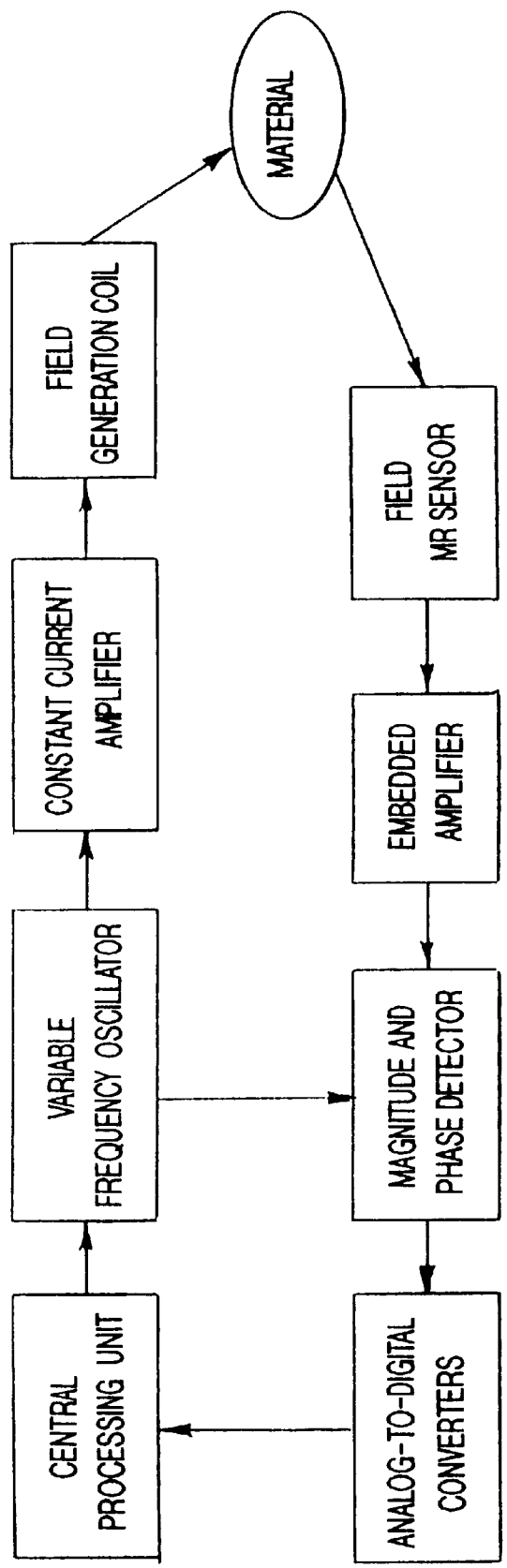
FIG. 6 is a diagrammatic illustration of the operational routine of the embodiment of FIGS. 5a and 5b.

Reference is made to FIGS. 5a and 5b, showing another embodiment of the detector apparatus 30, this embodiment employing solenoid induction but with the passive absolute field sensor configuration generally according to FIG. 1b. This embodiment is similar to the embodiment of FIGS. 2a and 2b with respect to magnetic field generation; however, the sensitive axis 52 of the GMR sensor 50 is disposed generally parallel to the principal axis 41 of the coil 40, and thus is substantially aligned with the applied magnetic field (25 in FIG. 1b), as indicated by the directional arrow of FIG. 5a. The GMR sensor 50 detects the absolute field resulting from the interaction of the applied field 25 with the induced field (26 in FIG. 1b). As indicated by reference to FIG. 6, after amplification by an embedded amplifier, both the magnitude and the phase of the resulting signal response from the GMR sensor 50 are detected by a magnitude and phase detector known in the art and then input, by way of dual analog-to-digital converters, to the CPU. In all the foregoing embodiments (FIGS. 2a, 2b, 4a, 4b, 5a and 5b), therefore, components are included whereby the responsive signal from the GMR sensor is processed directly, that is, the change in resistance in the GMR sensor is itself the signal providing the information regarding the condition of the material under test.

Figure 7A:
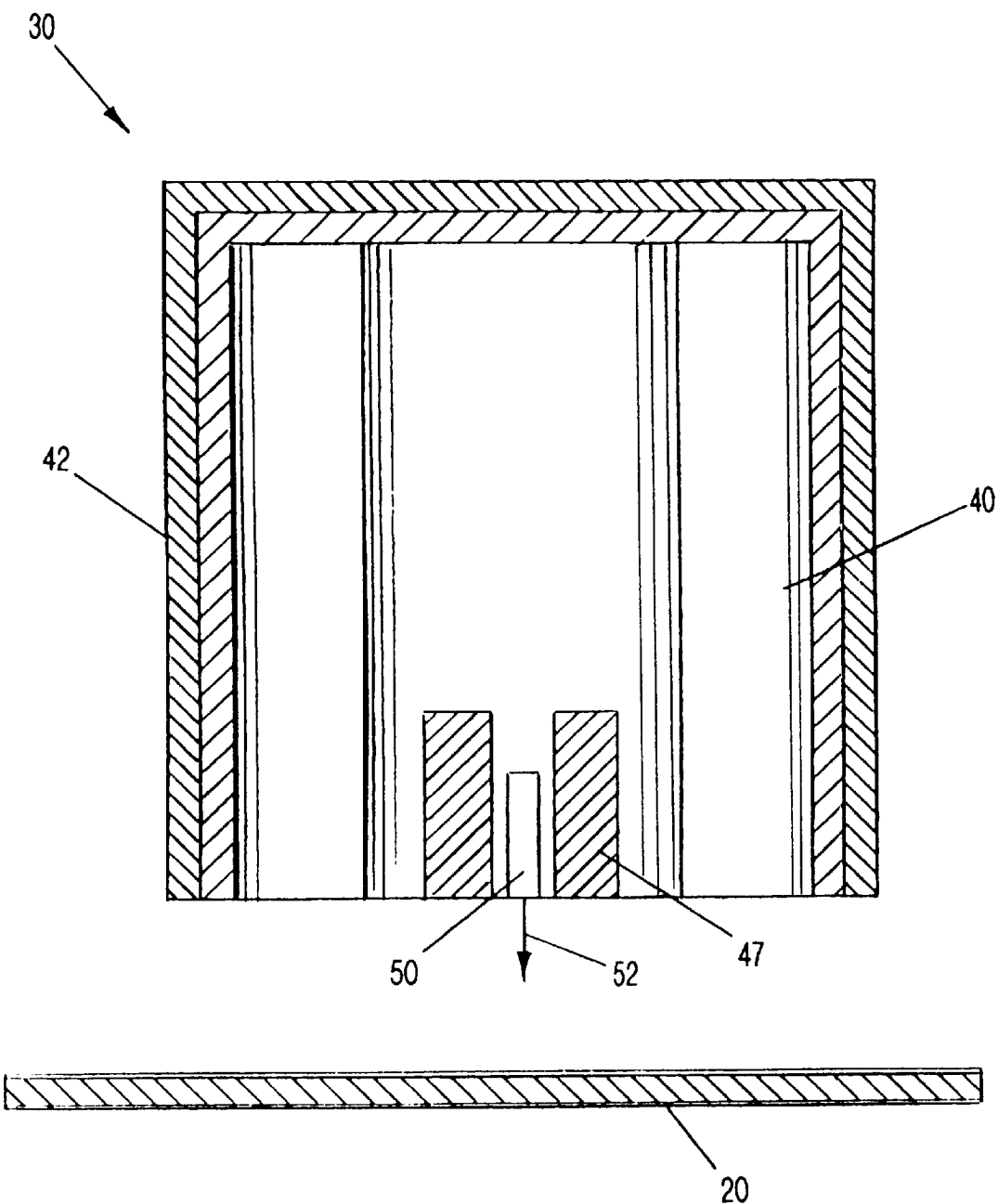
FIG. 7a is a side sectional view of a coil induction embodiment of the invention configured to perform absolute field sensing with active compensation for the magnetic field.
Figure 7B:
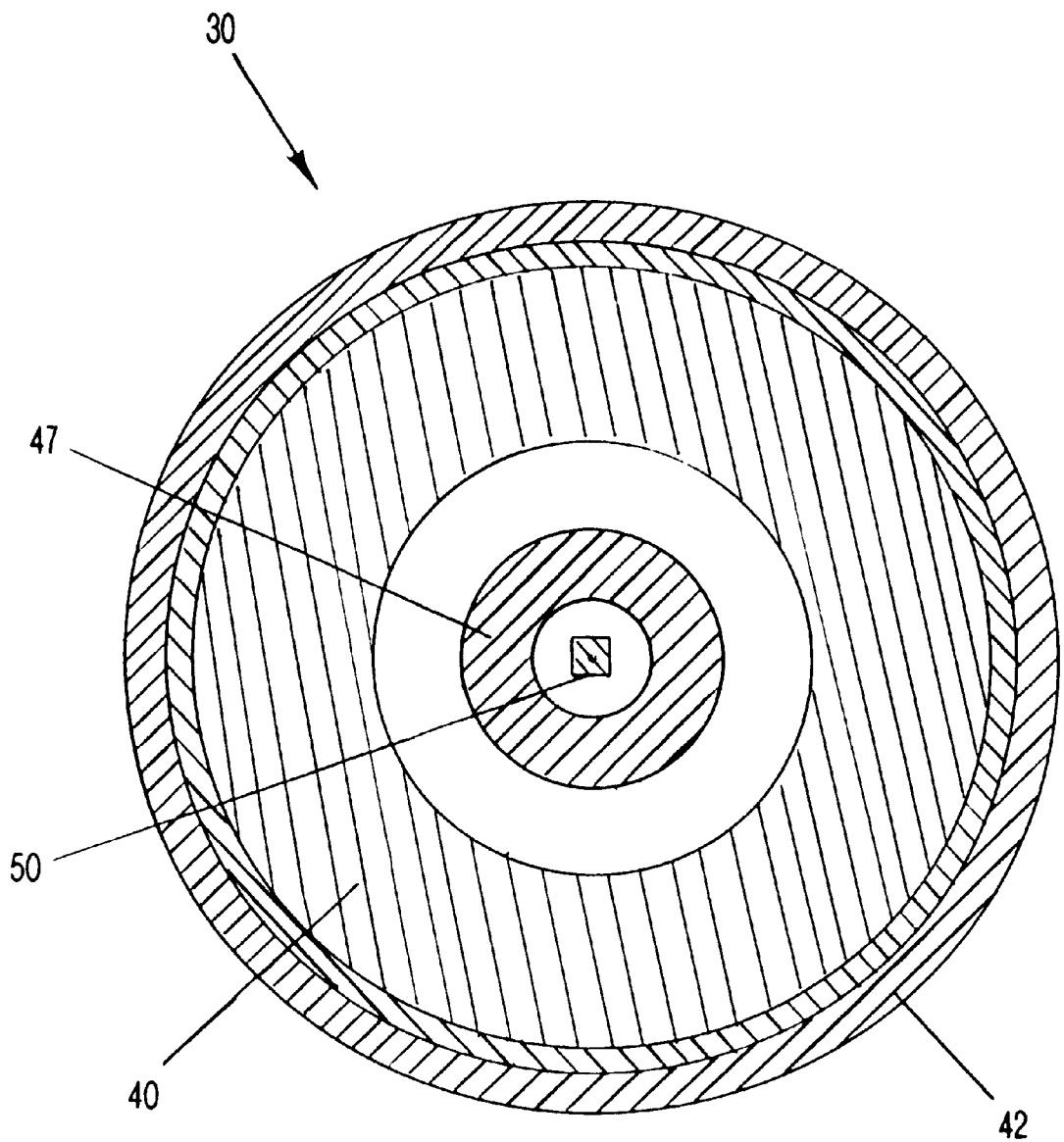
Figure 8:
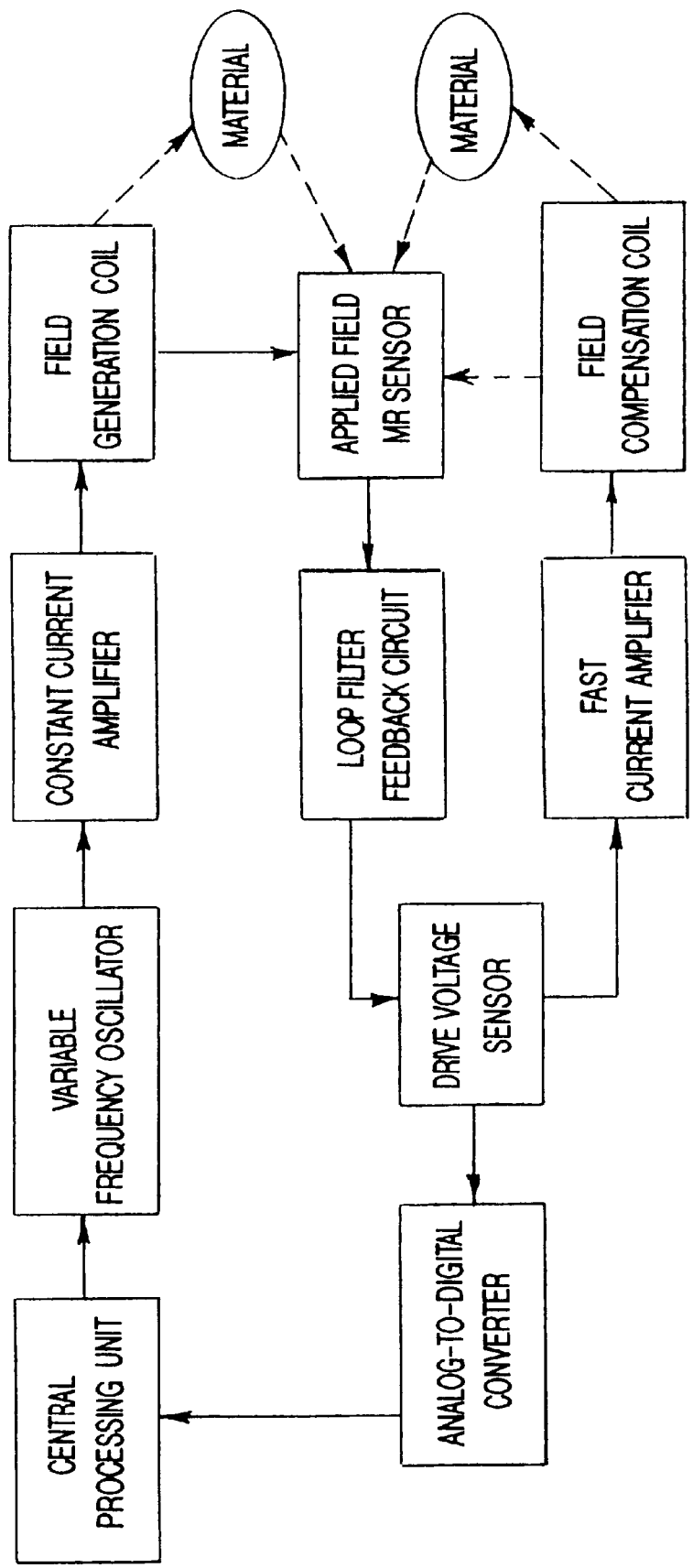
FIG. 8 is a diagrammatic illustration of the operational routine of the embodiment of FIGS. 7a and 7b.

FIGS. 7a and 7b show an alternative embodiment of the detector apparatus 30 employing solenoid induction with an absolute field configuration, and utilizing active compensation. The embodiment of FIGS. 7a and 7b is similar to the embodiment of FIGS. 5a and 5b in that it measures the absolute field; this embodiment differs, however, in the method of measuring the absolute field. The signals from the GMR sensor 50 are not processed directly, but rather are indirectly detected and processed. The embodiment of FIGS. 7a and 7b uses a pair of coils 40, 47. The field compensation coil 47 preferably is disposed coaxially within the field generation coil 40, and the field compensation coil 47 is disposed around the GMR sensor 50 so that the sensor 50 is interior to both coils 40, 47. The sensitive axis 52 of the GMR sensor 50 is parallel or collinear with the principal axis of the field generation coil 40. The outer field generation coil 40 generates the applied interrogation field, which is detected by the GMR sensor 50. Reference also to FIG. 8 illustrates that the output from the GMR sensor 50 is fed to a loop-filter feedback circuit, which drives a fast current amplifier by means of a drive voltage sensor. The fast current amplifier in turn drives a field compensation coil 47, which generates a compensation field counteractive to the applied field such that the effective field sensed by the GMR sensor 50 is zero. In this embodiment, the analog-to-digital converter monitors the driving voltage input to the fast current amplifier, rather than the signal output from the GMR sensor 50. This active compensation embodiment allows much larger interrogation field amplitudes to be used, relative to the previously described passive embodiments.

Figure 9A:
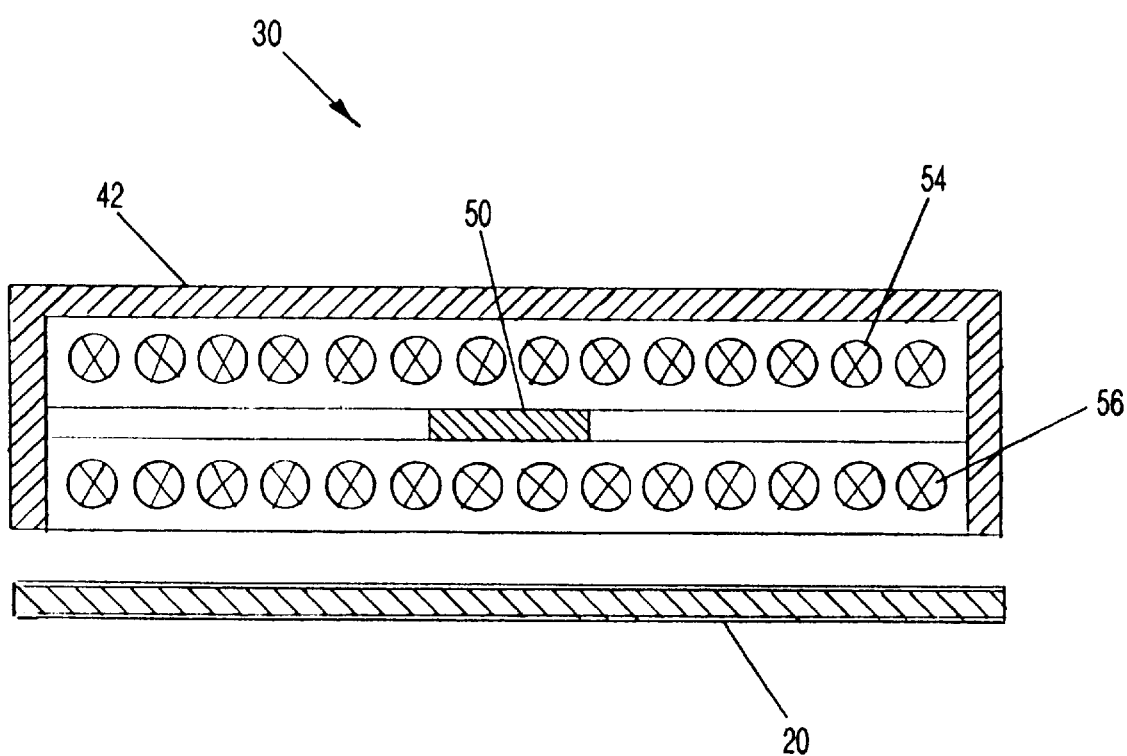
FIG. 9a is a side sectional view of a sheet induction embodiment of the apparatus of the invention with active field compensation.
Figure 9B:
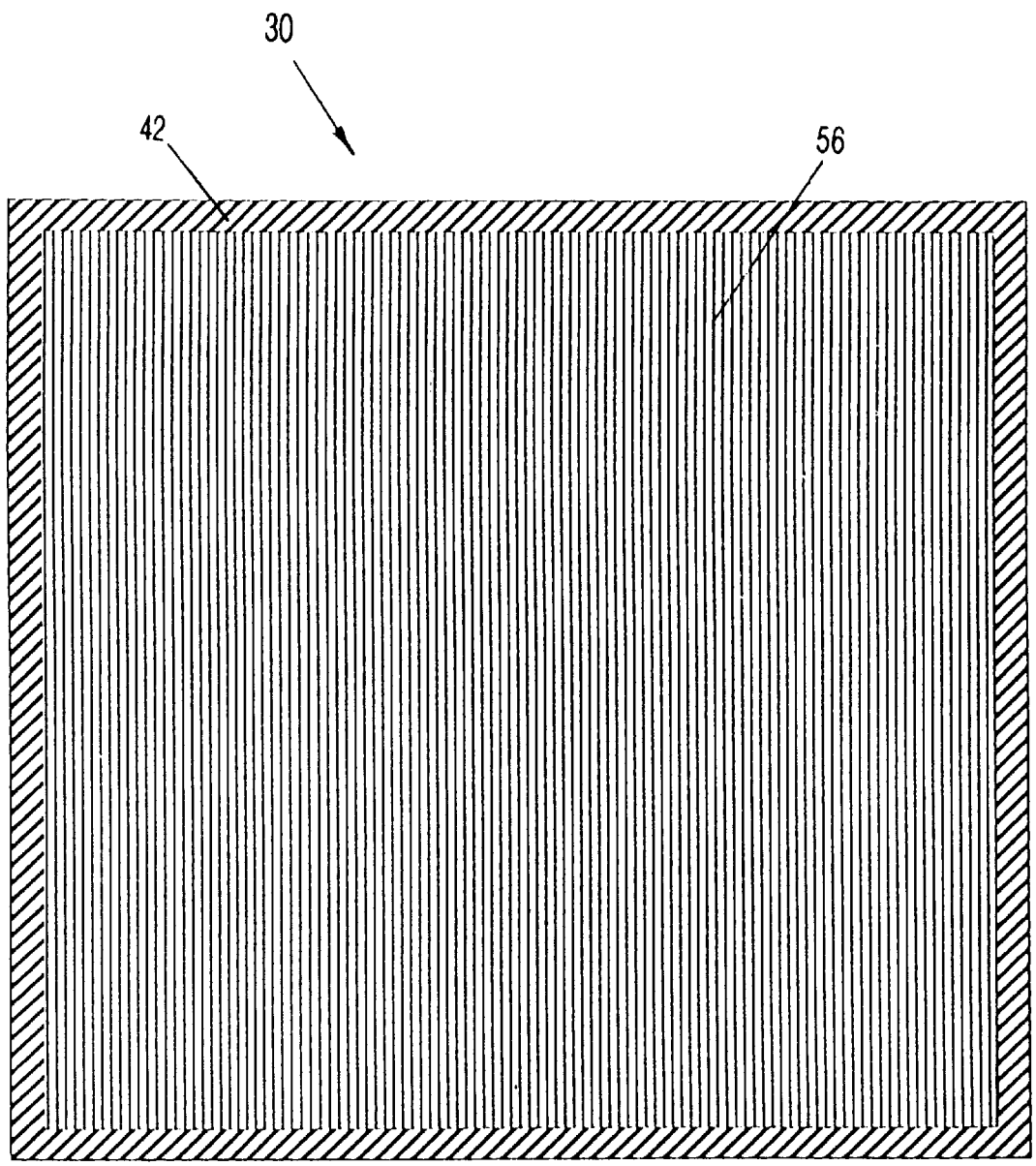
Figure 10:
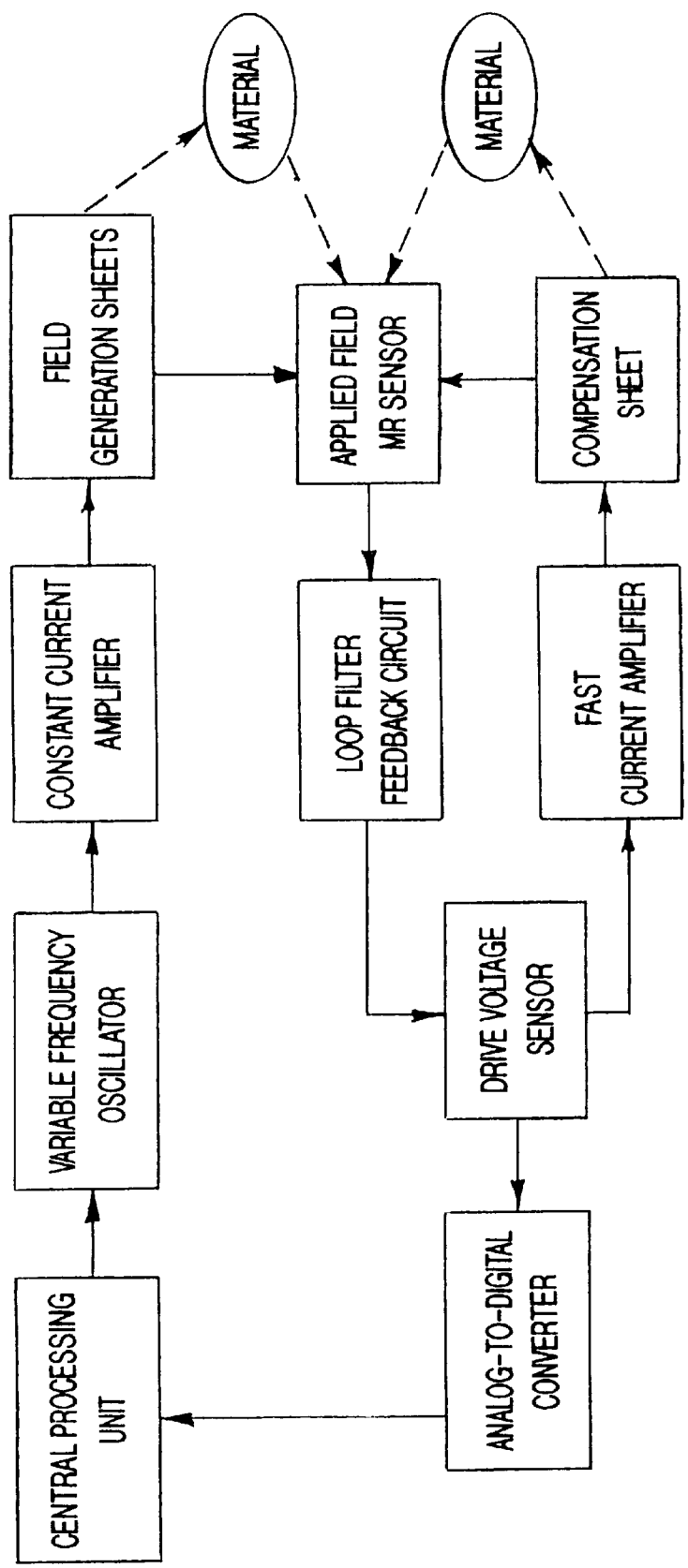
FIG. 10 is a diagrammatic illustration of the operational routine of the embodiment of FIGS. 9a and 9b.

FIGS. 9a and 9b show a detector apparatus 30 employing sheet induction with active compensation. Electronically, this embodiment of detector 30 is similar to the embodiment of FIGS. 7a and 7b, but this embodiment employs a current sheet induction scheme. The GMR sensor 50 is disposed generally parallel between a substantially planar conductive drive sheet 54 and a substantially planar conductive compensation sheet 56 generally parallel thereto. Current (indicated by the circled Xs in FIG. 9a) is driven, through both the drive sheet 54 and the compensation sheet 56, generating two magnetic fields, an applied field and a compensative field, respectively. These resulting magnetic fields add in the regions exterior to the GMR sensor 50, and counteract to substantially cancel each other in the layer containing the GMR sensor 50. When the detector apparatus 50 is placed against the MUT 20, the fields from both the sheets 54, 56 are applied, causing eddy-currents in the MUT 20 which generate an induced field which counteracts or opposes the compensative field in the compensation sheet 56 more strongly than the applied field of the drive sheet 54. This asymmetrical opposition results in an incomplete cancellation of the fields at the GMR sensor 50. Combined reference is made to FIGS. 9a, 9b and 10, shows that the net magnetic field is detected by the GMR sensor 50, whose responsive signal drives a loop-filter compensation circuit similar to the circuitry of the FIG. 8 embodiment. A fast current amplifier drives the compensation sheet 56, such that the effective field sensed by the GMR sensor 50 is zero. The analog-to-digital converter monitors the driving voltage input to the fast current amplifier, rather than the output from the GMR sensor 50, and the current to the compensation sheet 56 is modified to cancel substantially the net field at the GMR sensor 50 and the input voltage to the fast current amplifier is monitored by the A/D converter, whereby the signal response of the GMR sensor 50 is only indirectly processed to yield final NDE data. In these embodiments employing active field compensation, therefore, the response signal from the GMR is not directly processed into information regarding the material under test; rather, a looped feedback circuit is employed whereby the response signal (i.e. change in resistance) output by the GMR sensor drives the compensative field, and a voltage input necessary to counteract or compensate the applied field is monitored to provide the necessary data regarding the material under test. Nevertheless, the apparatus of the invention indirectly processes the signaled changes in the resistance of the GMR sensor to accomplish the task of detecting changes in the induced field.

Figure 11A:
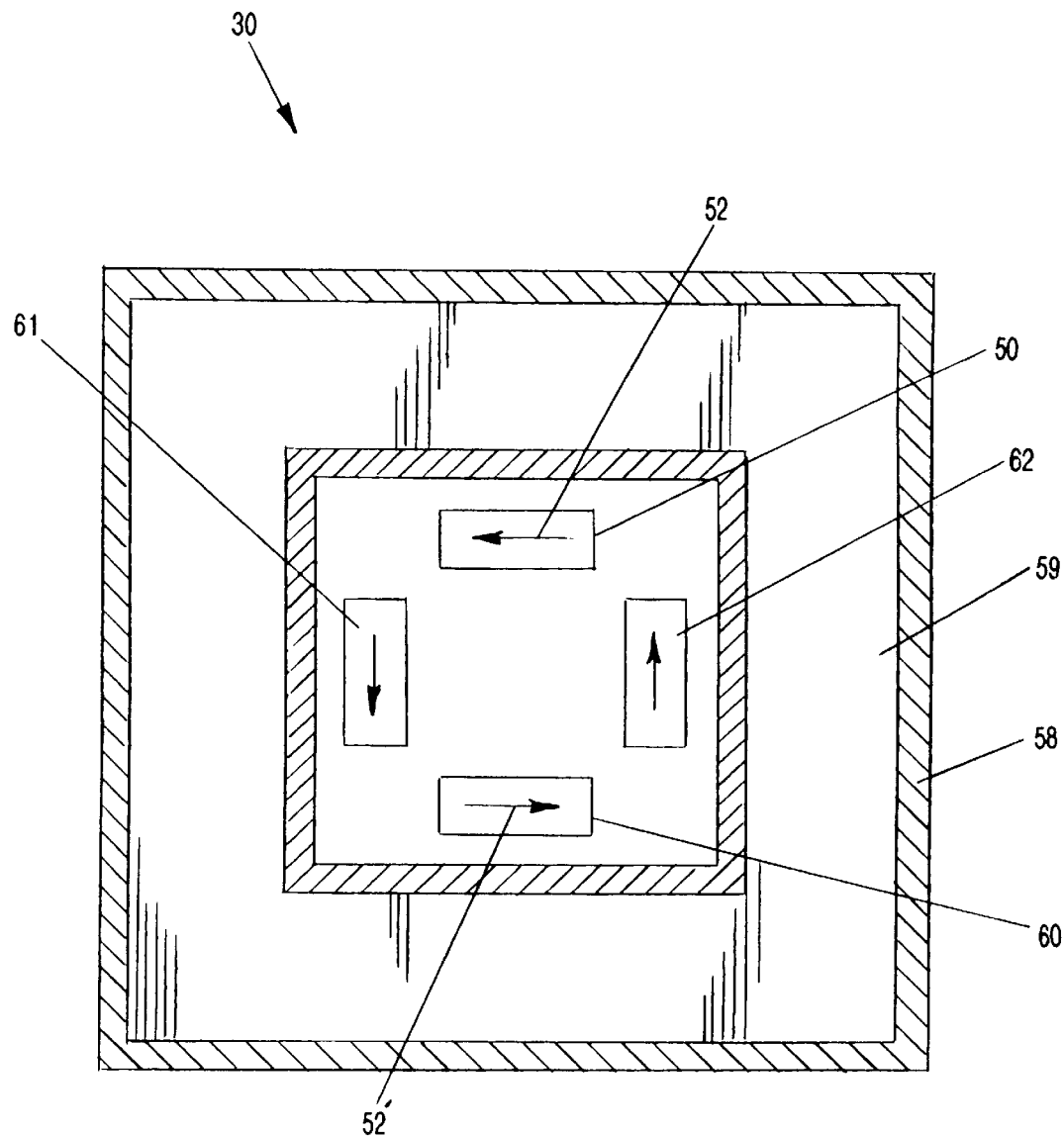
FIG. 11a is a top sectional view of a ferromagnetic induction embodiment of the apparatus of the invention configured to perform curl sensing.
Figure 11B:
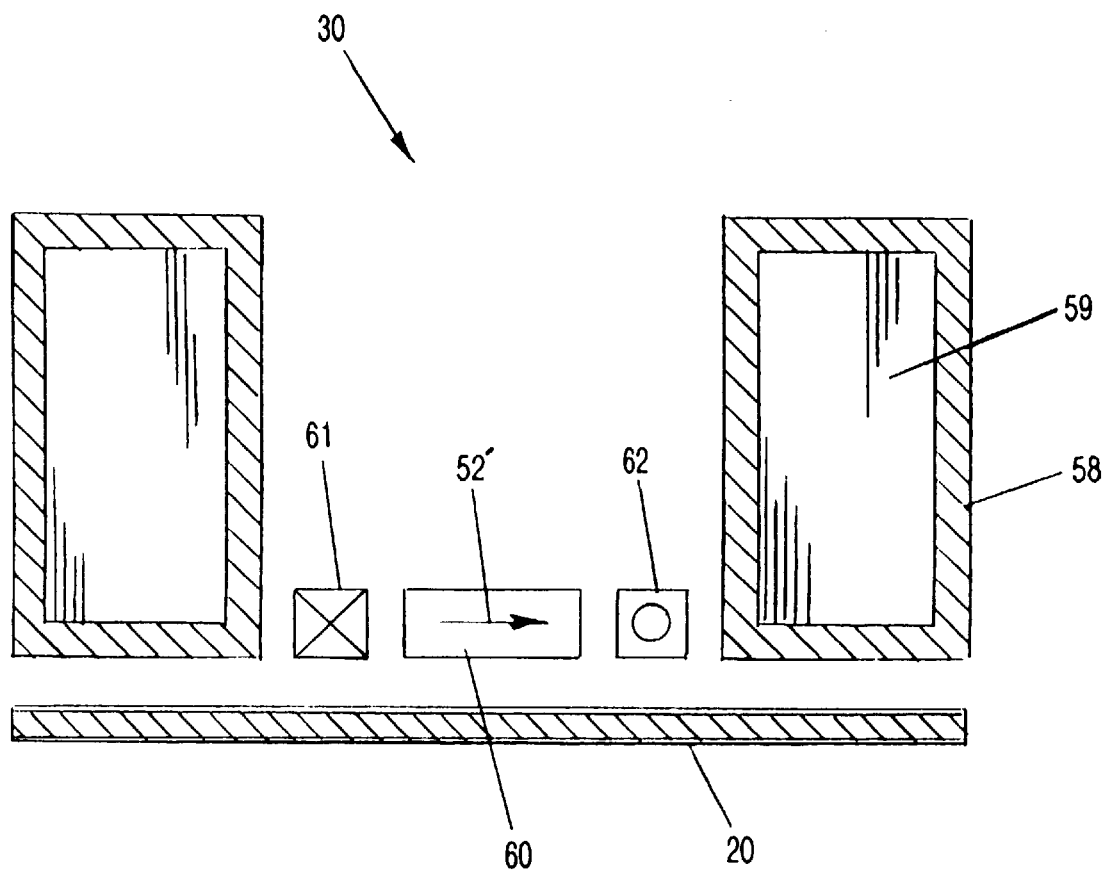
Figure 12:
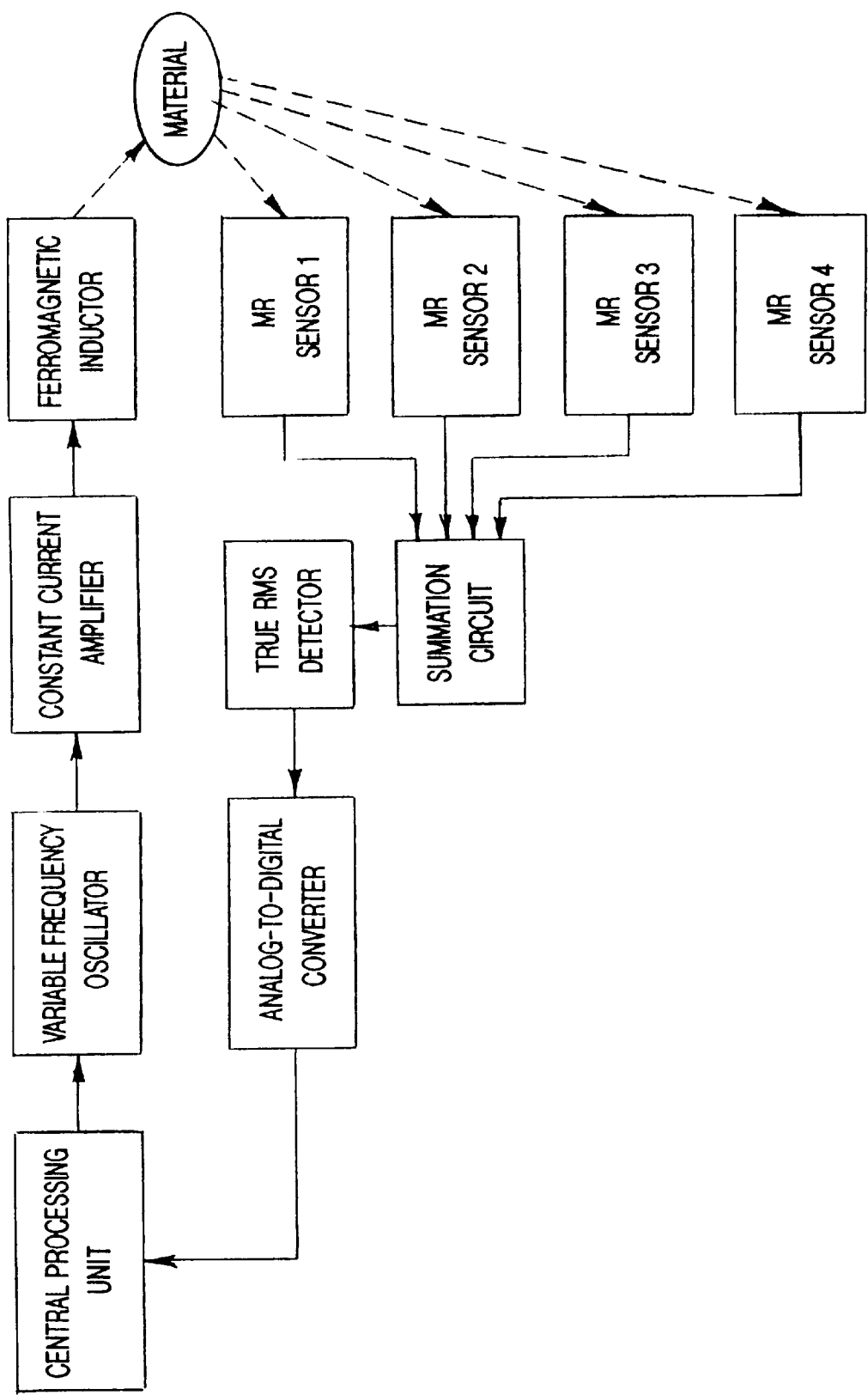
FIG. 12 is a diagrammatic illustration of the operational routine of the embodiment of FIGS. 11a and 11b.

When performing NDE on ferrous materials, including steels, it is advantageous to replace coil or solenoid induction with ferromagnetic induction. FIGS. 11a, 11b and 12 show a detector apparatus 30 with ferromagnetic induction and configured to sense field curl. In this embodiment, a constant current amplifier drives a ferromagnetic inductor including a winding of wire 58 wrapped around a ferrite core 59, thereby generating a large applied magnetic field.

Alternatively, a rotating, scanning magnetic field may be generated in the MUT if ferrite 59 is a toroid perpendicular to the surface having both longitudinal and toroidal windings 58. By suitably driving the separate windings, the principal axis of the resultant field in the MUT 20 can be oriented at, or swept through, any angle relative to the sensor positions.

In this usage, the MUT 20 is ferrous and responds to the applied field with a "mirror" induced field. The interactions between the two fields are detected using at least two, preferably four or more, GMR sensors 50, 60, 61, 62 surrounded by the ferrite core 59. Within the component of the net field sensed by each GMR sensor 50, 60, 61, or 62 is the curl generated by a large, changing electric field within the ferrite core 59. Reference to FIG. 12 illustrates that an instrument system utilizing a CPU controls the variable frequency oscillator, the output of which controls a constant current amplifier which in turn feeds electrical current to the ferromagnetic inductor. The inductor induces fields in the ferrous material under test 20. The GMR sensors 50, 60, 61, 62 are geometrically disposed such that the sensitive axes 52, 52' of at least two opposing sensors (e.g. 50, 60) are parallel, as seen in FIG. 11a. As illustrated by FIG. 12, induced fields in the MUT 20 affect the GMR sensors 50, 60, 61, 62, which send signals to a summing circuit of known construction which adds the signals from the GMR sensors, whereby optimal sensitivity is achieved regardless of the positional relation of any defect in the MUT 20 with respect to the GMR sensors 50, 60, 61, 62. The summed signal is sent to a true RMS detector that conditions the signal voltages coming from the summation circuit, providing a voltage corresponding to the magnitude of the defect detected. An A/D converter converts the voltage corresponding to signal magnitude to a digital word readable by the CPU. The CPU performs automated data analysis on the sensor data for use in NDE, manufacturing or other applications.

Figure 13A:
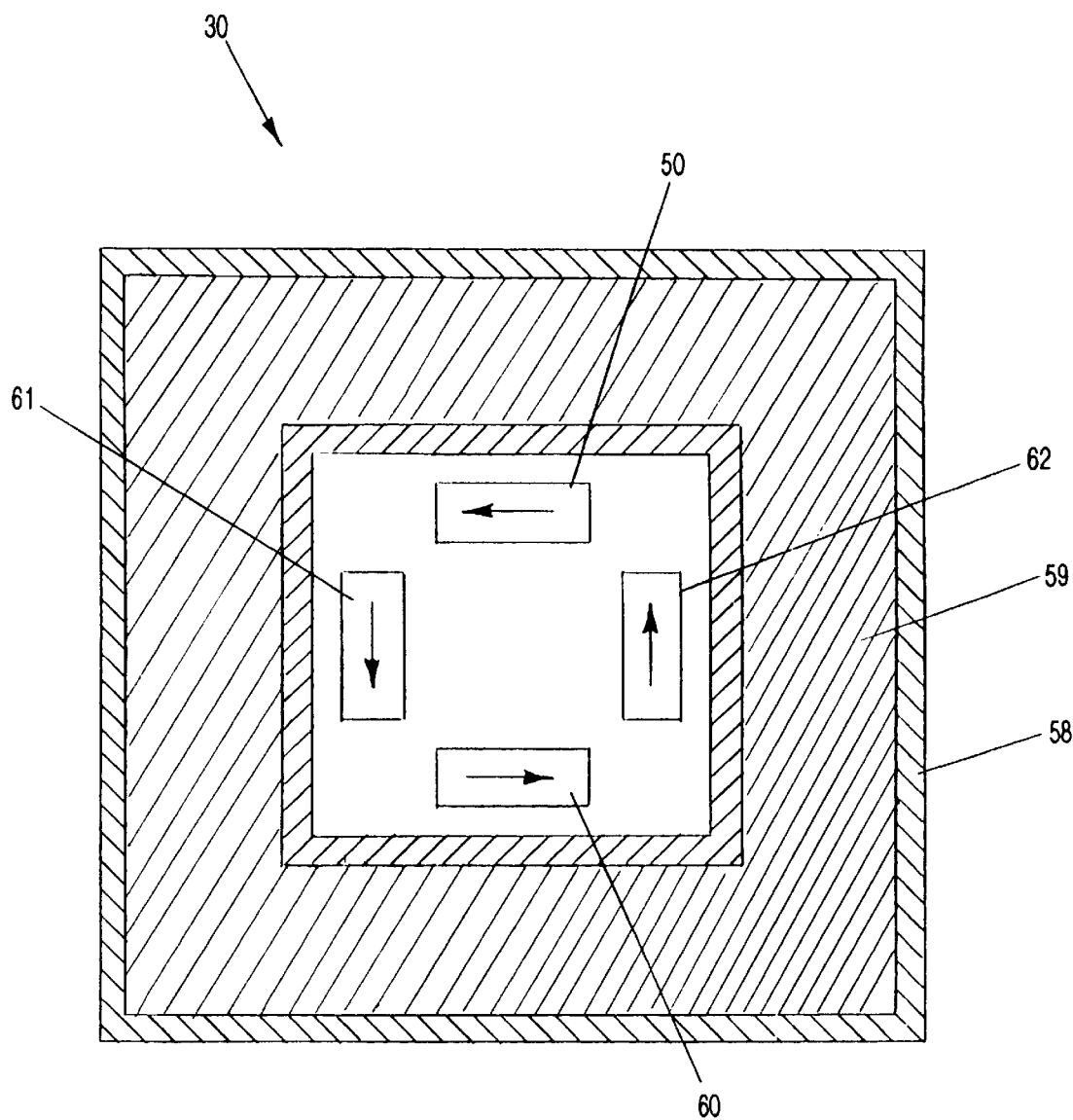
FIG. 13a is a top sectional view of a ferromagnetic induction embodiment of the apparatus of the invention configured to perform dual-differential field sensing.
Figure 13B:
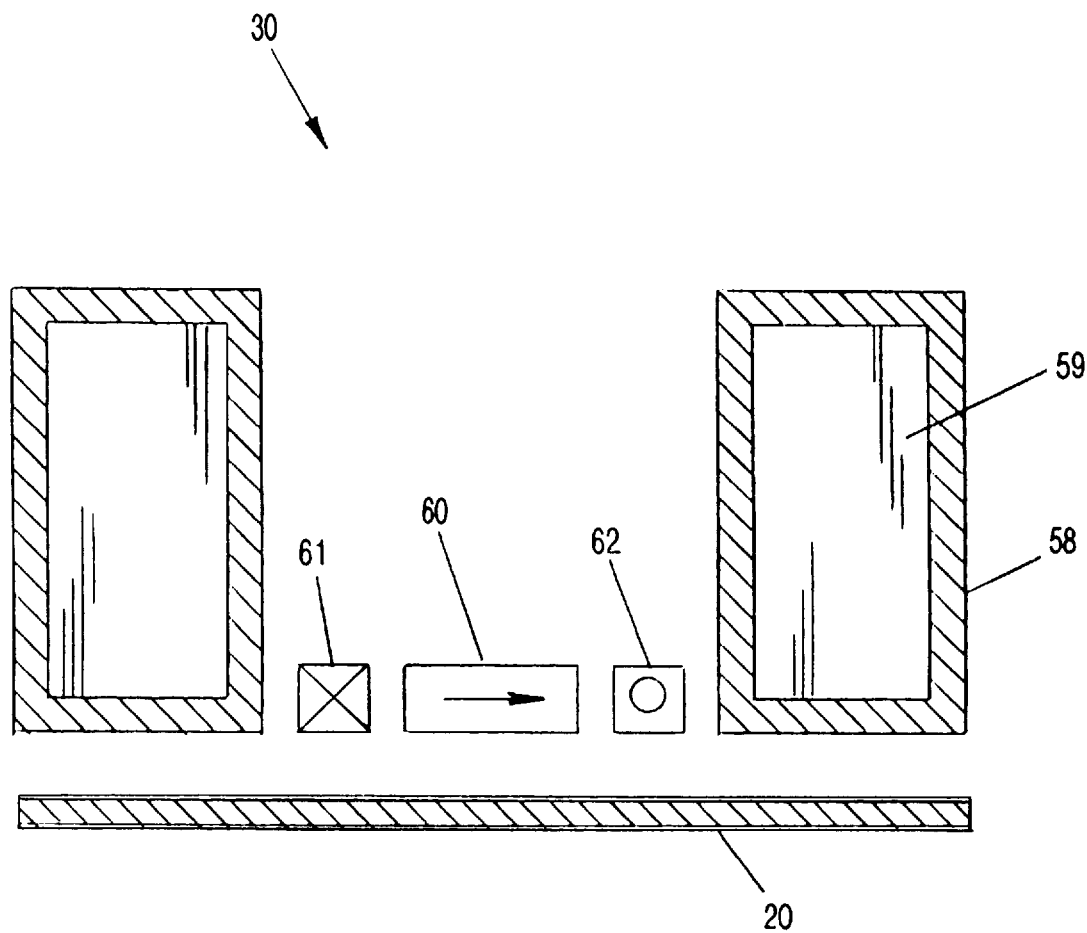
Figure 14:
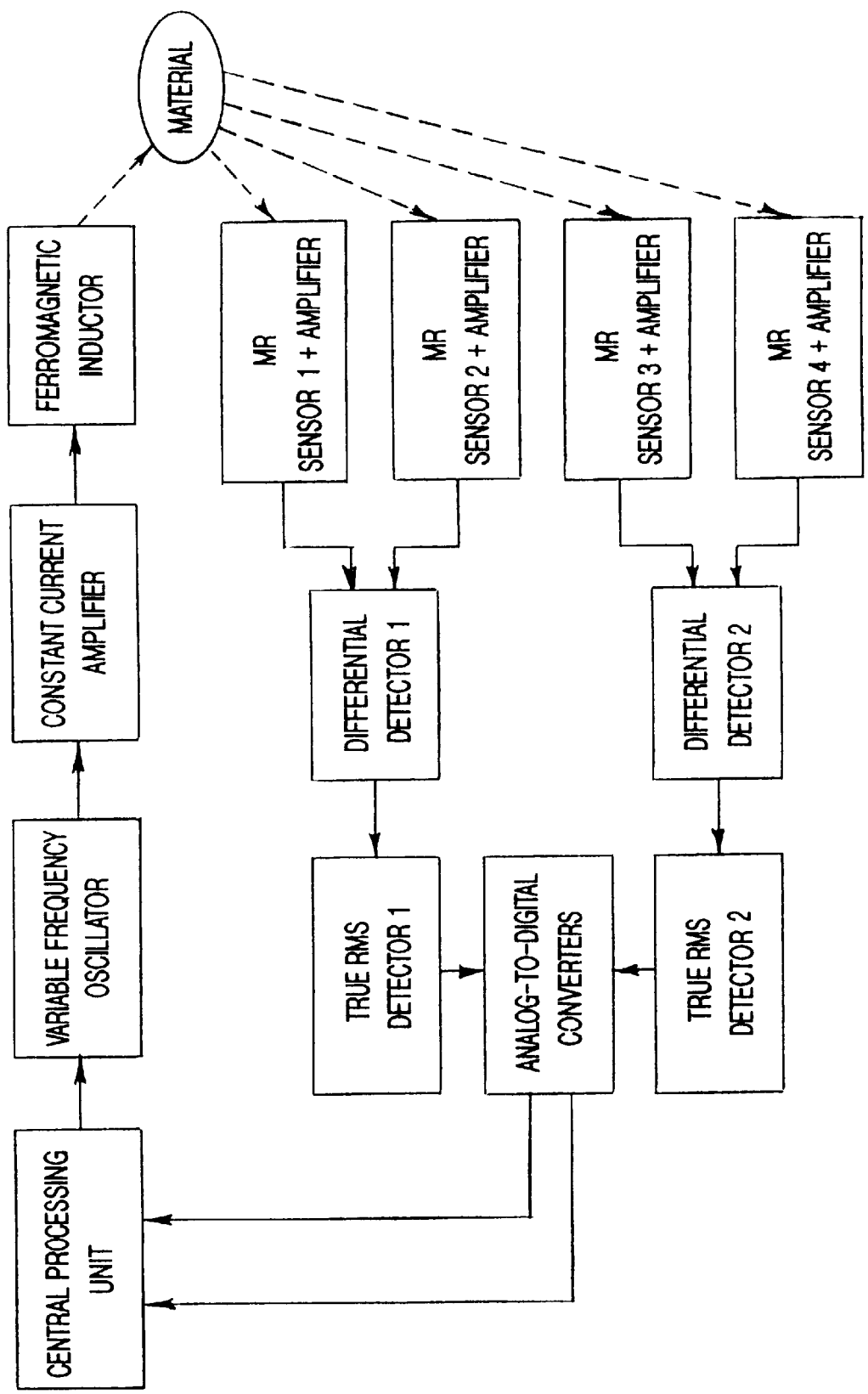
FIG. 14 is a diagrammatic illustration of the operational routine of the embodiment of FIGS. 13a and 13b.

FIGS. 13a, 13b and 14 show a ferromagnetic induction detector apparatus 30 of the invention, with dual-differential detection. The physical portion of this embodiment is very similar to the embodiment of FIGS. 11a and 11b. A difference between the embodiment of FIGS. 11a and 11b and this embodiment is in the GMR sensor signal processing. Instead of summing the outputs of all of the GMR sensors 50, 60, 61, 62, the dual-differential configuration of the apparatus 30 uses differential detection to sense the differences in responsive signal magnitude from opposing pairs of GMR sensors, such as pairs of sensors 50, 60 and 61, 62 in FIG. 13a, to provide specific information regarding geometric symmetry within the MUT 20. With the sensitive axes of at least one pair, and preferably two pair, of opposing sensors disposed generally parallel, any discontinuity in the MUT 20 results in an incomplete cancellation between the paired sensors 50, 60 or 61, 62.

FIG. 14 shows that signals from opposing pairs of sensors 50, 60 and 61, 62 are input into respective differential detectors of known construction, each of which in turn provides input into a separate True RMS detector. Reference to FIG. 14 also illustrates that a CPU controls the variable frequency oscillator, the output of which controls a constant current amplifier which in turn feeds electrical current to the ferromagnetic inductor. The inductor induces fields in the ferrous material under test 20. The GMR sensors 50, 60, 61, 62 are placed in a geometry such that the sensitive axes of at least two, and preferably two or more pairs, of opposing sensors (e.g. 50, 60 and 61, 62) are parallel to one another (FIG. 13a). The magnetic fields induced in the MUT 20 cause the GMR sensors 50, 60, 61, 62, which are configured in a dual differential mode, to output responsive signals. Amplified output signals from the opposing pairs of GMR sensors (sensors 50, 60 and 61, 62 in FIG. 13a) are fed to the differential detector circuits which output the difference in magnitude between the associated pair of GMR sensors 50, 60 or 61, 62. If, for example, both sensors of a pair 50, 60 or 61, 62 respond equally to spurious noise, this configuration of the detector apparatus 30 cancels the output due to noise. This embodiment of the detector apparatus 30 also provides information concerning the geometry of defects in the MUT 20, since the larger size or closer proximity of a defect to any single one of the GMR sensors results in a larger signal from that sensor and consequently a larger differential signal for the corresponding sensor pair 50, 60 or 61, 62. Another advantage of this embodiment over four or more single GMR sensors is that the noise cancellation properties of the configuration make it possible to discern smaller defects in the MUT 20.

FIG. 15 shows a two-dimensional array of a plurality of GMR sensors 50 on a single substrate 64. Such an array may be fabricated using a variety of techniques, with the GMR sensor elements 50 having spin valve, tunnel junction or other device configurations. The sensor elements 50 may be formed on solid substrates such as silicon wafers, or flexible substrates such as polyimide. Data from the array of GMR sensors 50 is read by computer for the purpose of making two dimensional images of a object in a magnetic field. Such a two-dimensional array of GMR sensors 50 may be used in any of the embodiments of the detector apparatus 30 depicted in FIGS. 3–14.

FIG. 16 shows that a three dimensional array of GMR sensor elements 50 may be embedded in a sandwich structure having a plurality of layers. As with the FIG. 15 disclosure, such an array can be fabricated using a variety of techniques with the GMR sensors 50 having spin valve, tunnel junction or other device configurations. The GMR sensor elements 50 can be formed on a plurality of two or more (three shown in FIG. 16) solid substrates 64, 66, 67 such as silicon wafers, or flexible substrates such as polyimide. Data from the arrays is read by computer for the purpose of making three dimensional images of an object in a magnetic field.

Figure 17:
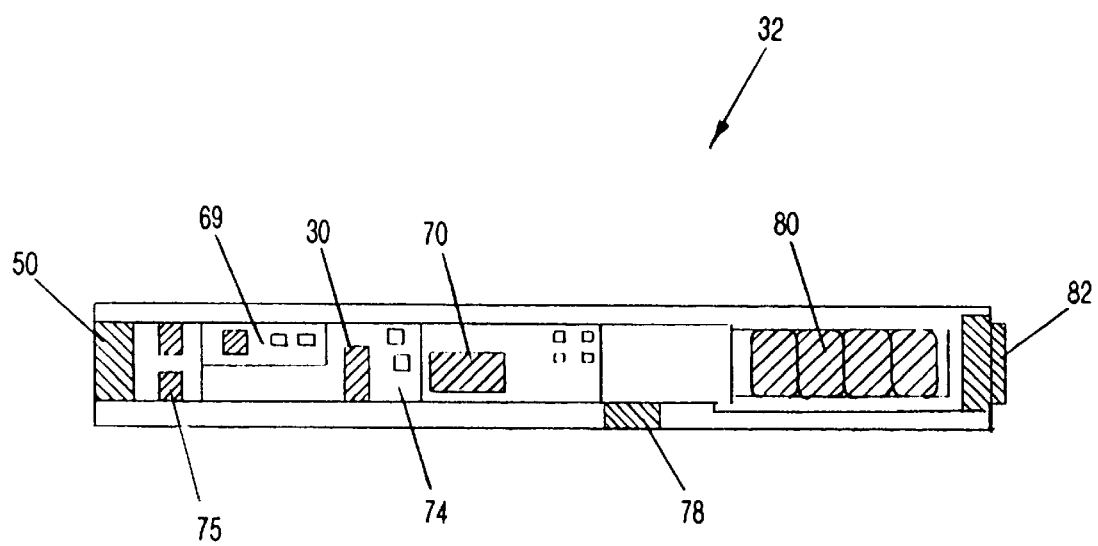
FIG. 17 is a side sectional view of a hand-held embodiment of a single-channel detector apparatus in a self-nulling configuration according to the present invention.

Reference is made to FIG. 17, showing a single channel NDE detector apparatus 32 based on GMR sensors using the self-nulling configuration. A GMR sensor 50 is used for detection of magnetic fields. A central processing unit (CPU) 70 controls an oscillator and amplifier 69 which drive a coil for the induction of magnetic fields in the MUT 20. The sensor 50 responds to the magnetic fields induced in the MUT and outputs an electrical signal that is fed to a preamplifier and signal conditioning amplifier 75 and then an analog filter section 74. The amplified and conditioned sensor signal is fed to an A/D converter and then to the CPU 70 for digital signal processing and data analysis. The CPU 70 sends data to a external computer using a serial port 78. The apparatus 32 also has visual LCD and audible outputs 82. The apparatus is run by rechargeable batteries 80 for portable operation.

INDUSTRIAL APPLICABILITY

The invention is further illustrated by the following non-limiting examples.

Fabrication of the Spin Valve Type GMR Sensors

Two spin valve GMR sensor arrays were fabricated on 2-inch diameter Silicon wafers. Small pieces were cleaved from each wafer to perform magnetic and transport characterization. The deposition parameters for both structures were nominally identical. The deposition layer thicknesses were as follows:

Si/Si/Ox/NiO (500 Å)/Co (5 Å)/NiFe (35 Å)/Cu (35 Å)/Co (5 Å)/NiFe (50 Å).

These layer thicknesses were chosen to create GMR sensors with the highest low field sensitivity. Magnetization curves and magneto-resistance curves for the two devices were made to evaluate the high field behavior in both the hard and easy (sensitive) axis directions as well as the low field behavior along the easy axis. The easy axis is defined by the field applied during the deposition. The highest GMR sensitivity occurs when the field is applied along the easy axis. However, the reversal along the easy axis occurs through domain wall motion and thus can be rather noisy.

A 4×4 array of GMR sensors was formed on each wafer by cutting shallow grooves in the surface with a diamond scribe. The sheet resistance was roughly 80 ohms per square. The inter-sensor resistance on the wafer was about 1000 ohms due to conduction through the silicon. This level of resistance is high enough to permit detection of the individual responses of the sensors while on the silicon substrate. The feasibility of a functional GMR sensor array on a single silicon substrate (e.g. as seen in FIG. 15) is thus demonstrated.

Individual GMR sensors approximately 1 cm on each side were cut form the silicon wafer. The characteristics of the individual sensors were measured using a shielded axial solenoid to produce magnetic fields with variable amplitude and frequency. The total resistance change from no field to full saturation averaged 6.08% with saturation at 4 Oe resulting in a sensitivity of 1.5%/Oe. In a bridge sensor configuration, the measured sensitivity was 4.44 mV/VOe with an element resistance of 41.3 ohms.

Wheatstone Bridge GMR Sensors

Other GMR sensors on a silicon substrate had multilayer sheet resistance of about 10 ohms per square, and resistor legs on silicon 2 microns across. These properties allow the construction of a 10K resistor in an area of 80 microns by 100 microns (using 2 micron lithography). The sensors were housed in an 8-pin surface mount SOIC package. Two of the more sensitive devices had resistance changes of 9.81% and 9.74% for the sense resistors with saturation at 15 Oe resulting in a sensitivity of 0.64%/Oe. At a nominal bridge bias voltage of 5V, the measured bridge sensitivity was 4.0 mV/VOe with an element resistance of 3.92K.

Figure 19:
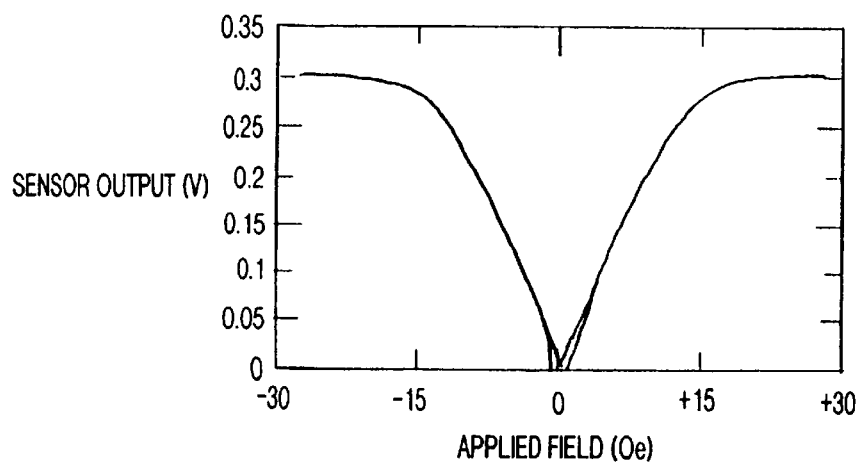
FIG. 19 graphically displays the plot of the giant magnetoresistance response for the material used to make a GMR sensor used in an embodiment of the apparatus of the invention.

A plot of the GMR response for the material used to make the sensors is shown in FIG. 19. The measurement was made with a four point probe, 5 volt bias.

The Wheatstone bridge is advantageous for DC measurements where a significant DC offset makes the measurement of small DC signals difficult. For AC measurements the DC offsets are easily eliminated with a simple filter. The impedance of the Wheatstone bridge itself can present problems with signal degradation, particularly at higher frequencies. Studies showed that signal quality was good up to approximately 1 MHZ with the Wheatstone bridge configuration.

The use of flux concentrators essentially increase the sensitivity of the GMR material by some concentration factor of from 2 to 100. The flux concentration factor is roughly equivalent to the length of one shield divided by the length of the gap between the shields. The use of tailored flux concentrators could substantially increase the low field sensitivity of GMR sensors designed specifically for NDE.

A variety of excitation coil geometries and GMR sensor orientations were evaluated. In general, aligning the sensitive axis of the GMR sensor with the primary axis of the applied excitation field produced eddy current-induced signal amplitude variations in a relatively large amplitude residual signal. By orienting the GMR sensor easy axis orthogonal to the primary axis of the applied field, similar amplitude changes were obtained while greatly reducing the residual signal amplitude. The Wheatstone bridge GMR sensors, while not of optimum configuration, were significantly easier to work with than bare GMR wafers, even though the latter type of GMR sensors were somewhat more sensitive. Therefore, the majority of the NDE measurements were obtained using a Wheatstone bridge configuration.

The output of the GMR sensor was fed to an amplifier circuit and data collected with a digital oscilloscope and a PC. This raw data consisted of voltages corresponding to the magnetic field strength at selected points on the material under test. The material test samples used during the development of the inventive apparatus consisted of sheets of aluminum and steel alloy selected to mimic components such as aircraft structures. The samples had cracks or cuts in the range of 0 to 100 $\mu$m and the GMR sensors were tested for the ability to locate these known "defects."

Figure 20:
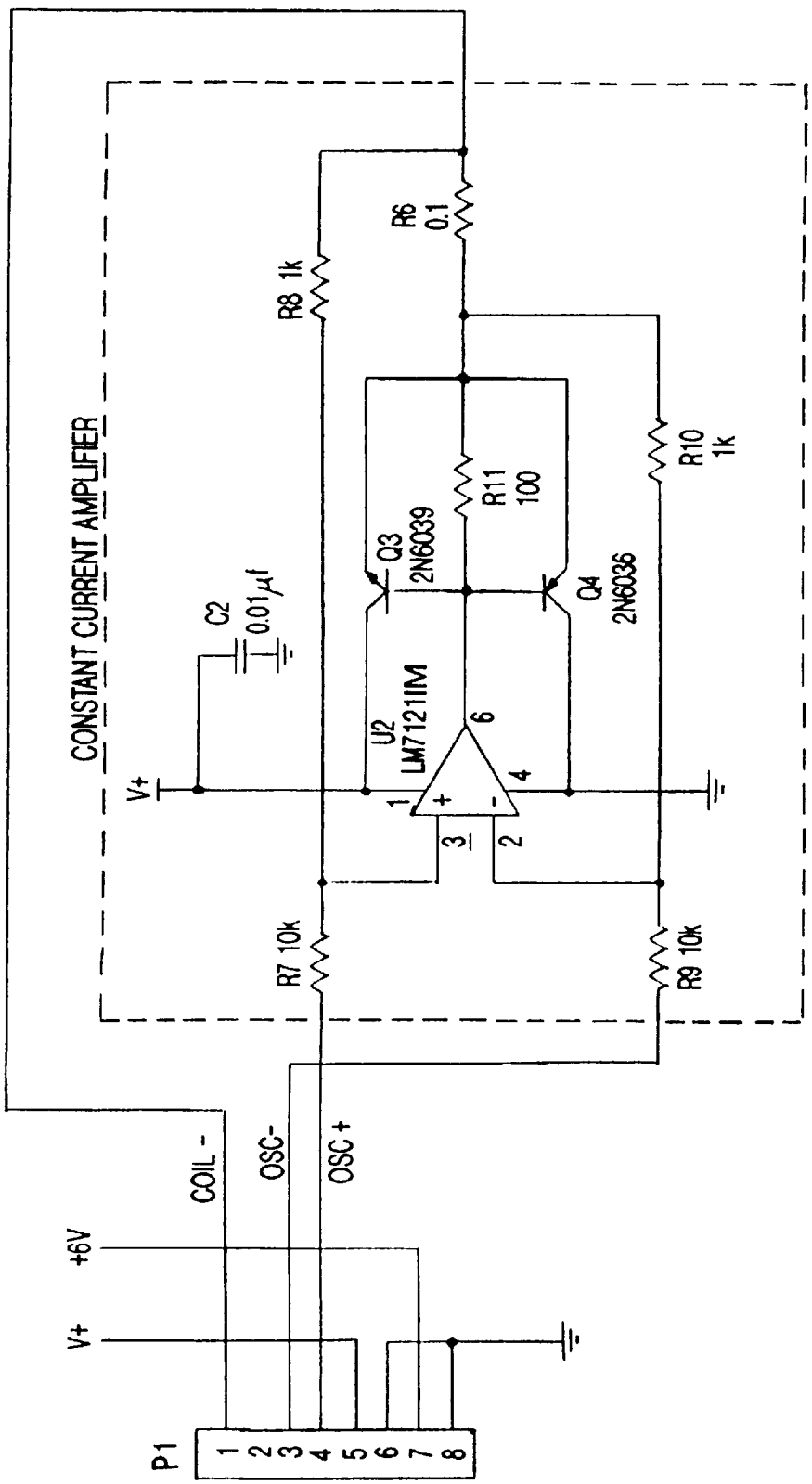
FIG. 20 is a schematic diagram of a circuit useable to operate the GMR sensor and induction field according to the invention.

The final GMR sensor optimized for the NDE measurements consisted of an Wheatstone bridge surrounded by a 55 $\mu$H excitation winding (90 turns, 6 layers pi wound, 7/32" ID, 0.42" OD, 0.12" high). The bridge and coil were placed on smooth, flat, defect-free sheets of 2024T3 aluminum and the coil driven to produce a 13 Oe peak field at 12 kHz. The bridge was orientated for minimum residual signal (i.e. generally perpendicular to the coil axis) and potted in place. The schematic of the circuitry utilized appears in FIG. 20.

Test Apparatus

Metal test samples were evaluated by affixing the material under test to a computer controlled, precision positioning mechanism and scanning the sample with the GMR sensor. The positioning mechanism controlled the distance between each measurement to ±10 $\mu$m.

The output of the GMR sensor was fed to an amplifier circuit and data collected with a digital oscilloscope and a personal computer (PC). This raw data consisted of voltages corresponding to the magnetic field strength at selected points on the test samples. The GMR sensor apparatus optimized for the NDE measurements consisted of a Wheatstone bridge sensor arrangement surrounded by a 55 $\mu$H excitation winding.

Test Samples

Figure 18:
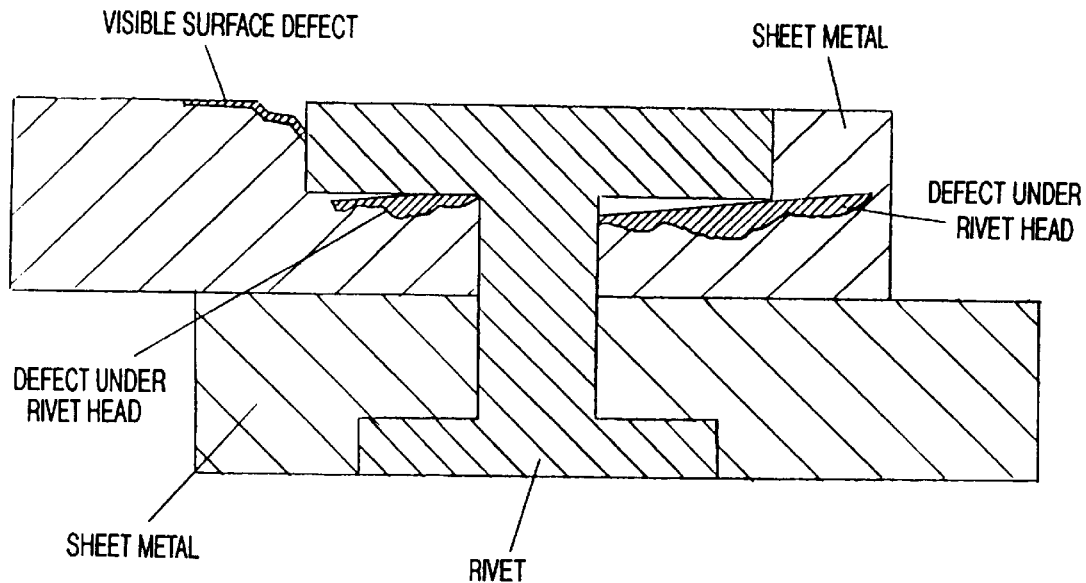
FIG. 18 is a side sectional view of a crack in an aluminum sheet hidden under a rivet head and detectable by practicing the present invention.

Tests were performed on 2024T3 aluminum. Sample plates 65 mils thick were cut using electric discharge machining (EDM) to form 100 $\mu$m wide slots (linear and arcuate). Additionally, 2024 aluminum alloy aircraft panels with known defects adjacent and under their 2024 "T" head rivets were obtained from the Federal Aviation Agency (FAA/AANC) NDE Center and Sandia National Laboratories. The rivet is a key site for incipient cracks in aircraft sections. These cracks are often covered by the head of the rivet. FIG. 18 is an illustration of a cross-section of a rivet site showing the types of cracks that occur.

NDE Testing

The prototype apparatus was evaluated for its ability to detect defects in a number of different materials including alloys of both aluminum and steel. Analysis was performed to determine the effects of the type of material under study, the dimensions and depth of the defect, and the effects of overlying metal on the detection of a defect.

A set of sample plates were cut using EDM to form a set of arcs with 1", ½", ¼", and ⅛" diameters. A similar set of test samples were cut with straight lines ½", ¼", ⅛", and 1/16" long. All of the cuts had a nominal width of 100 $\mu$m.

Figure 21:
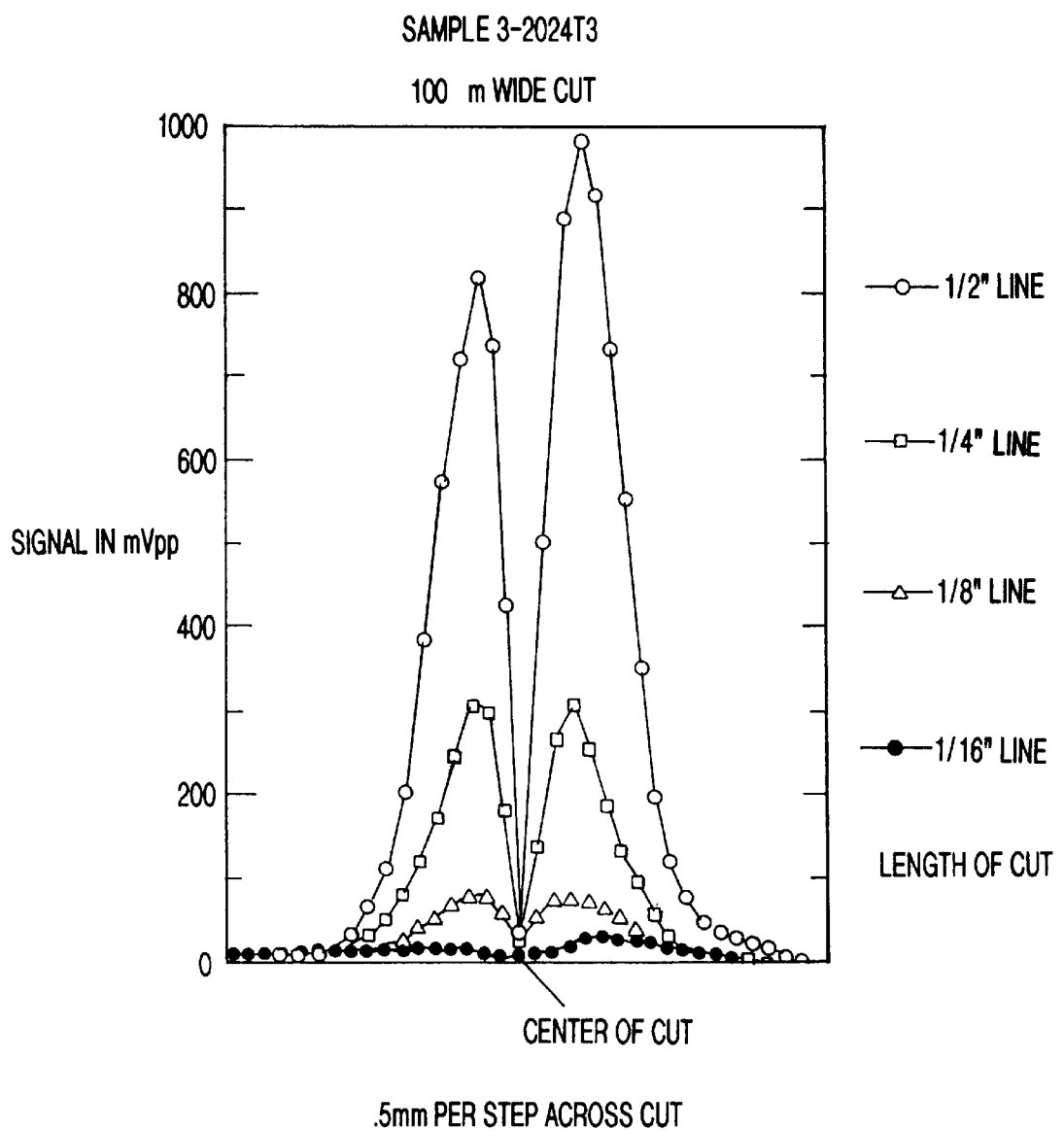
FIG. 21 graphically displays data obtained using a single channel embodiment of the apparatus of the invention to detect a straight line cut in a single metal sheet.
Figure 22:
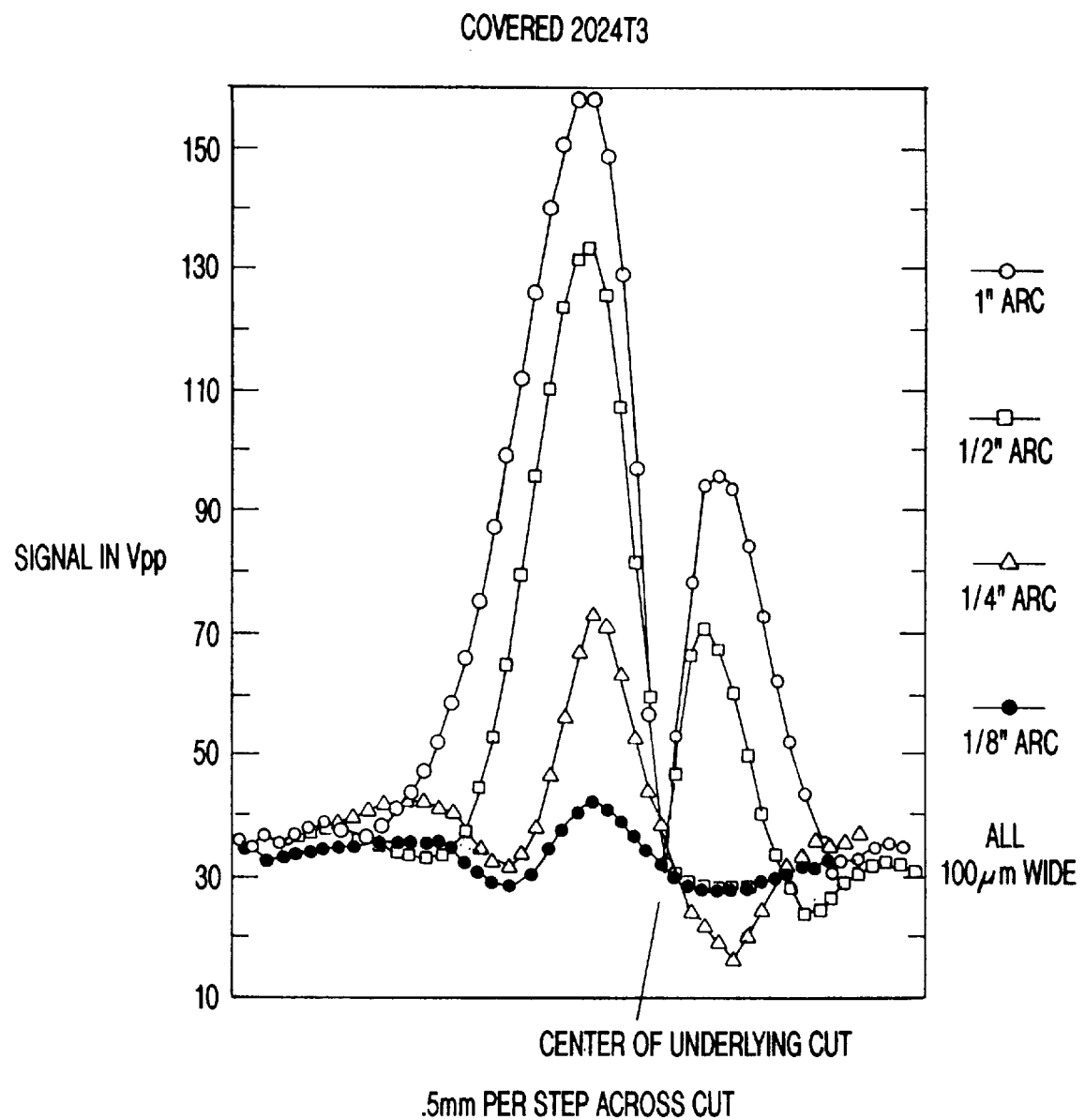
FIG. 22 graphically displays data obtained using a single channel embodiment of the apparatus of the invention to detect a crack hidden by an overlying metal sheet.

The GMR sensor and excitation winding were used to scan the surface of sheet metal test samples with either straight or arc-shaped cuts made with EDM. The results obtained by the scans are set forth graphically in FIGS. 21 and 22. FIG. 21 shows the sensor response for a 2024 aluminum sheet with 100 $\mu$m wide linear cuts of various lengths (1/16 inch, ⅛ inch, ¼ inch, and ½ inch). The baseline was extremely flat where no cut existed, and the signal to noise (S/N) ratio was in excess of 80 even for the ⅛-inch long cut. FIG. 22 shows the response for arc-shaped cuts in a covered panel, in similitude of the type of damage sought to be detected around rivets. All of the arc-shaped cuts were detectable in the lower 2024 aluminum panel, as indicated by the nadir in the graphical display.

In general, the signal amplitude from the GMR sensor system was extremely constant when no cut was present. As the edge of a cut was approached my the moving sensor, the locally induced magnet fields were concentrated and curved. This effect was detected by the GMR sensors and resulted in an increase in signal amplitude. By mapping the signal amplitude and position throughout a scan, it was possible to locate minute cuts in the material with a high level of confidence.

This method of defect detection was necessary during the invention development process. However, the S/N ratio was extremely high, indicating that the defect detector based on GMR technology could be quite simple yet highly dependable. One possible configuration for a practical field instrument would be a hand-held device that displayed a light when the signal intensity and signature indicated a defect (e.g., FIG. 17).

By way of further example, an aircraft material sample was obtained from an FAA facility consisting of two 2024 aluminum sheets [48 mils (1225 $\mu$m) and 74 mils (1870 $\mu$m)

thick] riveted together with 2024 aluminum rivets. The rivets had 0.0625 inch diameter shafts with 0.24 inch diameter heads and 1 inch nominal spacing between rivets.

Figure 23A:
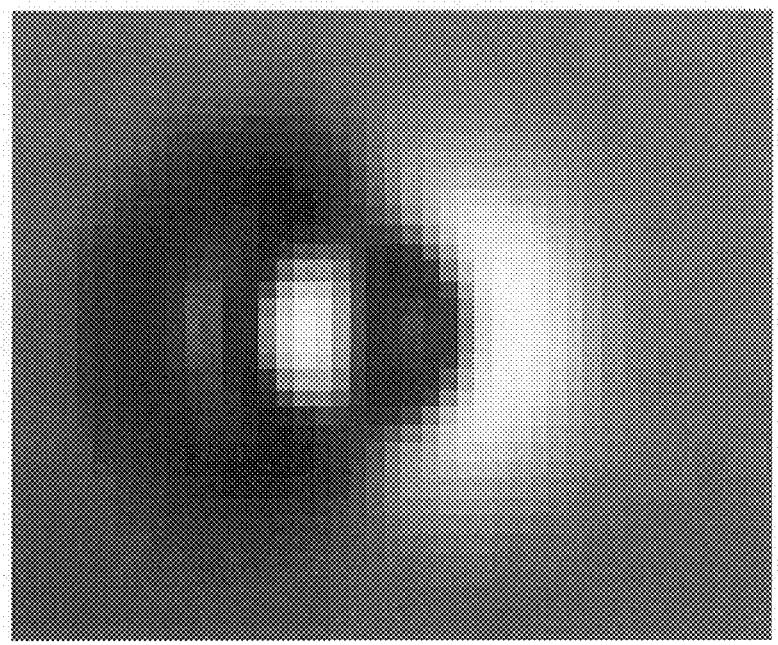
FIGS. 23a, 23b and 23c are digital two dimensional images of data obtained using a single channel embodiment of the apparatus of the invention used with an x-y positioning table, illustrating a normal rivet, an anomalous rivet, and a rivet covering two cracks, respectively.
Figure 23B:
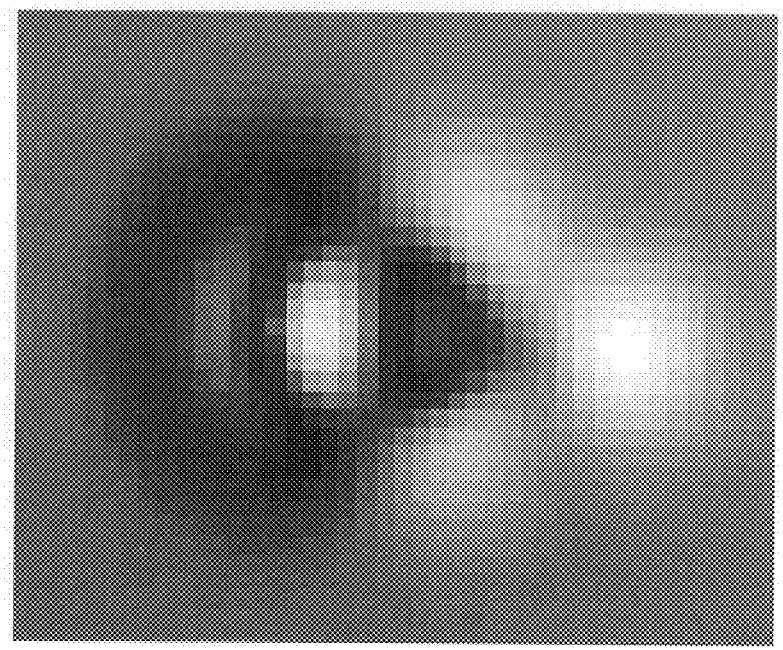
Figure 23C:
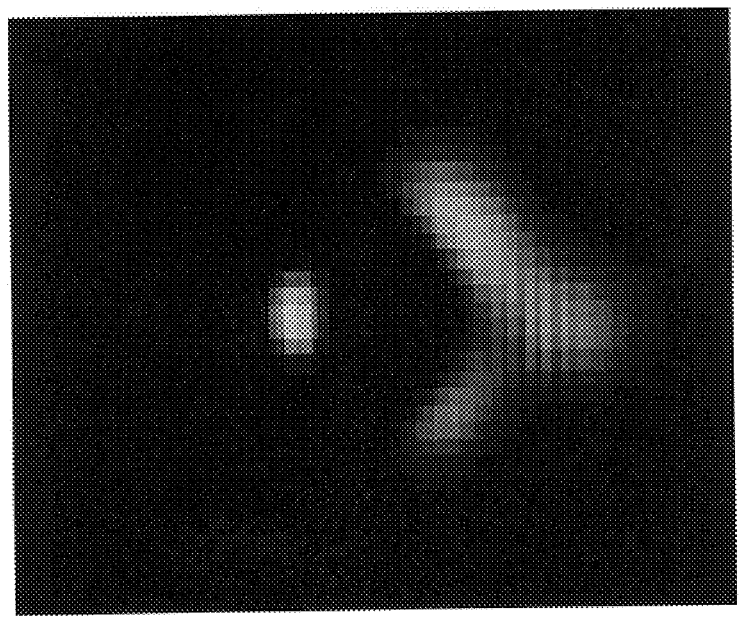

The area over and between the rivets was scanned using the apparatus of the invention with measurements taken at 500 $\mu$m increments. The data set formed a two dimensional grid. GMR sensor signal amplitude was plotted for each point on the grid. The resulting images of an inspection of a normal rivet and an anomalous rivet with two cracks are depicted in FIG. 23a and FIG. 23b, respectively. FIG. 21c shows a composite image resulting from the subtraction of the normal rivet image from the anomalous rivet image. The composite image of FIG. 23c provides a simple and intuitive assessment indication of the presence of a damaged part (rivet), illustrating the type of images and image enhancements obtainable with the invention.

As shown by FIGS. 21a, 21c, and 21c, the mechanical deformations and cracks associated with the rivets are clearly visible. The S/N ratio was extremely high with a very low noise level away from the riveted areas. The test showed that it is possible to image cracks that are underneath the rivet head and therefore undetectable with visual inspection.

Figure 24:
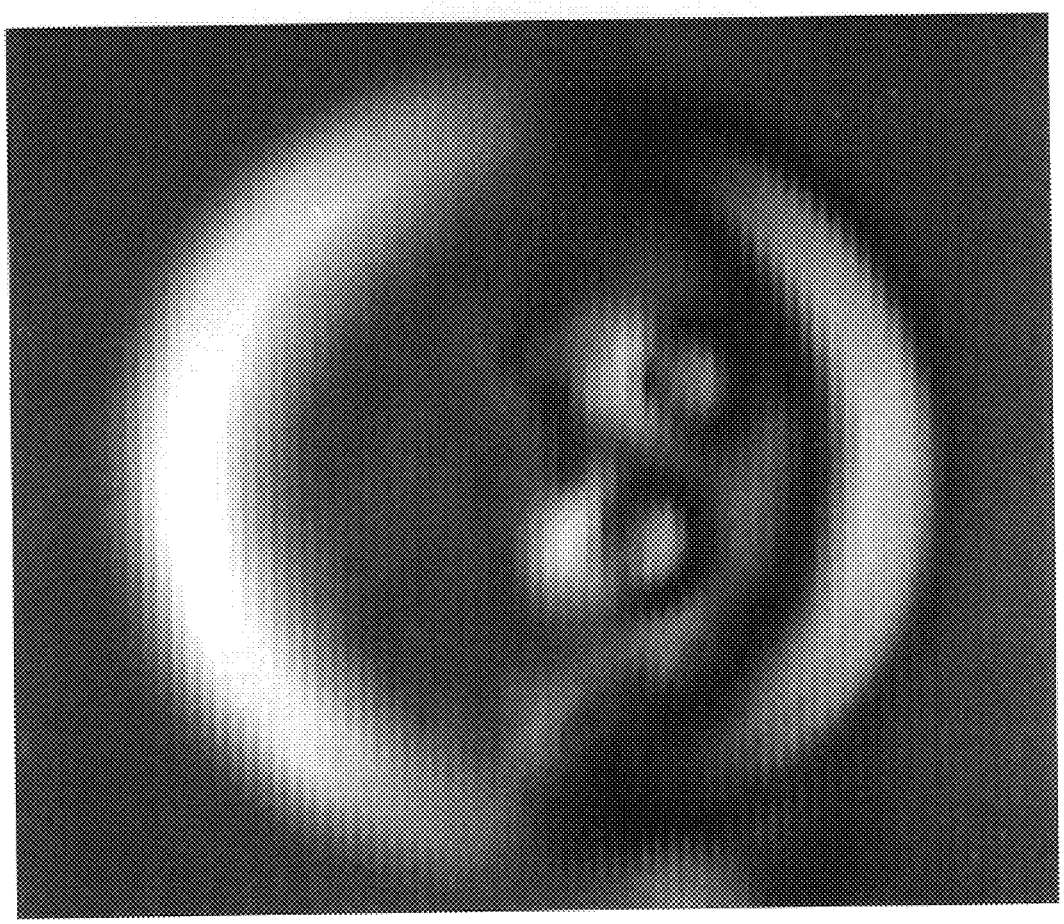
FIG. 24 is a digital two dimensional image of data obtained using a single channel embodiment of the apparatus of the invention used with an x-y positioning table, illustrating corrosion hidden inside an aluminum sample.

By way of further example, FIG. 24 depicts data from a single channel NDE corrosion detector taken with an x-y positioning table to yield a two dimensional image of corrosion hidden inside an aluminum sample.

The preceding examples can be repeated with similar success by substituting the generically or specifically described embodiments and operating conditions of this invention with equivalents thereof.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding provisional application, are hereby incorporated by reference.

We claim:

1. An apparatus for performing non-destructive evaluation of a material, said apparatus comprising:
    at least one magnetic field generator means, comprising an electrically conductive coil having a principal axis, for applying a magnetic field to the material, thereby inducing in the material an induced magnetic field;
    at least one giant magnetoresistance sensor, having a sensitive axis, proximate to said generator means and responsive to said induced magnetic field; and
    means, in communication with said at least one giant magnetoresistance sensor, for detecting changes in resistance in said at least one giant magnetoresistance sensor; wherein said sensitive axis is disposed substantially orthogonal to said principal axis of said coil, whereby said sensitive axis is unaligned with said applied magnetic field.

2. An apparatus according to claim 1 wherein said means for detecting changes in resistance in said at least one giant magnetoresistance sensor is selected from the group consisting of meters for measuring voltage, current, resistance, impedance and phase and analog-to-digital converters.

3. An apparatus according to claim 1 wherein said at least one giant magnetoresistance sensor is disposed substantially at an end of said coil.

4. An apparatus according to claim 1 wherein said at least one giant magnetoresistance sensor is disposed substantially interior to said coil.

5. An apparatus according to claim 1 wherein said at least one giant magnetoresistance sensor comprises a plurality of giant magnetoresistance sensors disposed upon at least one substrate.

6. An apparatus according to claim 5 wherein said substrate comprises a flexible material.

7. An apparatus according to claim 5 comprising a plurality of giant magnetoresistance sensors disposed upon a plurality of substantially parallel substrates.

8. An apparatus according to claim 1 wherein said means for detecting changes in resistance comprises means for directly processing signals from said at least one giant magnetoresistance sensor.

9. An apparatus according to claim 8 wherein said means for directly processing signals comprises:
    means for amplifying signals from said at least one giant magnetoresistance sensor;
    a true RMS detector in communication with said means for amplifying; and
    an analog-to-digital converter in communication with said RMS detector.

10. An apparatus according to claim 8 wherein said means for directly processing signals comprises:
    means for amplifying signals from said at least one giant magnetoresistance sensor;
    a magnitude and phase detector in communication with said means for amplifying; and
    an analog-to-digital converter in communication with said magnitude and phase detector.

11. An apparatus according to claim 1 further comprising means for generating a compensative magnetic field counteractive to said applied magnetic field; and
    a fast current amplifier, in communication with said at least one giant magnetoresistance sensor, for driving said means for generating a compensative magnetic field with a response from said at least one giant magnetoresistance sensor; wherein said means for detecting changes in resistance comprises:
    a voltage sensor in communication with said fast current amplifier; and
    means, in communication with said voltage sensor, for monitoring a drive voltage input into said fast current amplifier.

12. An apparatus according to claim 1 wherein said means for detecting changes in resistance comprises:
    circuit means for summing responses from said at least two giant magnetoresistance sensors;
    an RMS detector for receiving a voltage signal from said circuit means for summing; and
    converter means for converting said voltage signal into a digital signal.

13. An apparatus according to claim 1 wherein said means for detecting changes in resistance comprises:
    circuit means for detecting a difference in magnitudes of response from said at least two giant magnetoresistance sensors;
    an RMS detector for receiving a voltage signal from said circuit means for detecting; and
    converter means for converting said voltage signal into a digital signal.

14. An apparatus for performing non-destructive evaluation of a conductive material, said apparatus comprising:
    at least one magnetic field generator means for applying a magnetic field to the material, thereby inducing in the material an induced magnetic field;

at least one giant magnetoresistance sensor proximate to said generator means and directly responsive to said induced magnetic field, said sensor having a sensitive axis; and means for detecting changes in resistance in said at least one giant magnetoresistance sensor due to said induced magnetic field;

wherein said field generator means comprises a conductive winding wrapped about a ferrite core, and said at least one giant magnetoresistance sensor comprises at least two giant magnetoresistance sensors surrounded by said ferrite core with the sensitive axis of at least one of said giant magnetoresistance sensors disposed substantially parallel to a sensitive axis of at least one other of said giant magnetoresistance sensors.

15. An apparatus for performing non-destructive evaluation of a material comprising;

at least one magnetic field generator means for applying a magnetic field to the material, thereby inducing in the material an induced magnetic field;

a plurality of giant magnetoresistance sensors electrically interconnected in an array upon at least one substrate proximate to said generator means and responsive to said induced magnetic field;

means for detecting changes in resistance in said plurality of giant magnetoresistance sensors due to said induced field; and means for generating a compensative magnetic field counteractive to said applied magnetic field;

wherein said field generator means comprises a substantially planar conductive drive sheet and said means for generating a compensative magnetic field comprises a substantially planar conductive compensating sheet substantially parallel to said drive sheet, and wherein said giant magnetoresistance sensors are disposed between said drive sheet and said compensating sheet.

16. An apparatus according to claim 15 further comprising;

means for driving said means for generating a compensative magnetic field with a response from said giant magnetoresistance sensors.

17. An apparatus according to claim 16 wherein said means for driving said means for generating a compensative magnetic field comprises:

a fast current amplifier in communication with said giant magnetoresistance sensors; and a voltage sensor in communication with said fast current amplifier; and further comprising means, in communication with said voltage sensor, for monitoring a drive voltage input into said fast current amplifier.

18. An apparatus according to claim 15 wherein current driven through said drive sheet and said compensating sheet generates an applied magnetic field from said drive sheet and a compensating field from said compensating sheet, which fields add exteriorly to the location of said giant magnetoresistance sensors and substantially cancel each other at the location of said giant magnetoresistance sensors.

19. An apparatus according to claim 18 wherein when said apparatus is placed against the material, said fields from said sheets cause eddy currents in the material which generate an induced field which counteracts said compensating field more than said driving field, resulting in an incomplete cancellation of the fields to create a net field at the location of said giant magnetoresistance sensors.

20. An apparatus according to claim 19 wherein said net magnetic field is detected by said giant magnetoresistance sensors, said sensors generating a responsive signal for driving a loop-filter compensation circuit.

21. An apparatus according to claim 20 wherein said loop filter compensating circuit comprises:

a fast current amplifier for driving said compensation sheet such that the effective field detected by said giant magnetoresistance sensors is zero; and an analog-to-digital converter for monitoring a driving voltage input to said fast current amplifier.

22. An apparatus according to claim 15 wherein said means for detecting changes in resistance comprises means for directly processing signals from said giant magnetoresistance sensors.

23. An apparatus according to claim 22 wherein said means for directly processing signals comprises:

means for amplifying signals from said giant magnetoresistance sensors;

a true RMS detector in communication with said means for amplifying; and an analog-to-digital converter in communication with said RMS detector.

24. An apparatus according to claim 22 wherein said means for directly processing signals comprises:

means for amplifying signals from said giant magnetoresistance sensors;

a magnitude and phase detector in communication with said means for amplifying; and an analog-to-digital converter in communication with said magnitude and phase detector.

* * * * *